(12) United States Patent
Chai et al.

(10) Patent No.: US 9,603,941 B2
(45) Date of Patent: Mar. 28, 2017

(54) METHOD OF PREPARING DENDRITIC DRUGS

(76) Inventors: Minghui Chai, Mt. Pleasant, MI (US); Schengzhuang Tang, Mt. Pleasant, MI (US)

( * ) Notice: Subject to any disclaimer, the term of this patent is extended or adjusted under 35 U.S.C. 154(b) by 3002 days.

(21) Appl. No.: 11/653,548

(22) Filed: Jan. 16, 2007

(65) Prior Publication Data

US 2007/0190151 A1 Aug. 16, 2007

Related U.S. Application Data

(60) Provisional application No. 60/761,439, filed on Jan. 24, 2006.

(51) Int. Cl.
*A61K 9/14* (2006.01)
*A61K 47/48* (2006.01)

(52) U.S. Cl.
CPC .................. *A61K 47/481* (2013.01)

(58) Field of Classification Search
CPC .................................................... A61K 47/481
See application file for complete search history.

(56) References Cited

U.S. PATENT DOCUMENTS

| | | | |
|---|---|---|---|
| 5,945,100 A | 8/1999 | Fick | |
| 5,965,119 A | 10/1999 | Greenwald et al. | |
| 6,194,543 B1 * | 2/2001 | Florence et al. | 530/300 |
| 6,225,352 B1 * | 5/2001 | Horwell et al. | 514/617 |
| 6,280,745 B1 | 8/2001 | Flore et al. | |
| 6,296,842 B1 | 10/2001 | Jaworowicz et al. | |
| 6,432,423 B1 | 8/2002 | Maignan | |
| 6,458,347 B1 | 10/2002 | Sugawara et al. | |
| 6,468,519 B1 | 10/2002 | Uhrich | |
| 6,475,495 B1 | 11/2002 | Maignan | |
| 6,576,222 B2 | 6/2003 | Platzek et al. | |
| 6,600,010 B2 | 7/2003 | Mao et al. | |
| 6,608,168 B1 | 8/2003 | Ng et al. | |
| 6,613,807 B2 | 9/2003 | Uhrich | |
| 6,623,729 B2 | 9/2003 | Park et al. | |
| 6,623,730 B1 | 9/2003 | Williams et al. | |
| 6,623,764 B1 | 9/2003 | Sokoll et al. | |
| 6,689,350 B2 | 2/2004 | Uhrich | |
| 6,706,892 B1 | 3/2004 | Ezrin et al. | |
| 6,756,037 B2 | 6/2004 | Greenwald et al. | |
| 6,790,437 B2 | 9/2004 | Malik et al. | |
| 6,838,528 B2 | 1/2005 | Zhao | |
| 6,861,066 B2 | 3/2005 | Van De Casteele | |
| 6,864,350 B2 | 3/2005 | Harris | |
| 6,913,760 B2 | 7/2005 | Carr et al. | |
| 6,942,877 B2 | 9/2005 | Vogt et al. | |
| 2001/0007666 A1 | 7/2001 | Hoffman et al. | |

(Continued)

OTHER PUBLICATIONS

Crespo et al, Peptide and Amide Bond-Containing Dendrimers, Chem. Rev., 2005, 105, 1663-1681.*

*Primary Examiner* — Paul Dickinson

(57) ABSTRACT

Synthetic design of drug-incorporated novel dendrimer structures for quantitatively controlled drug delivery. The dendritic drugs have better control and thus a quantitative drug release can be obtained. There are no prior art dendritic drugs that control release both sequentially and quantitatively like the dendritic drugs disclosed herein. The dendritic drugs are formed by incorporating multiple same type drug units or more than two different drug types into a dendritic cascade structure to form a dendrimer drug.

17 Claims, 18 Drawing Sheets

(56) References Cited

U.S. PATENT DOCUMENTS

| | | |
|---|---|---|
| 2001/0011109 A1 | 8/2001 | Balogh et al. |
| 2002/0000681 A1 | 1/2002 | Gupta et al. |
| 2002/0022012 A1 | 2/2002 | Cooper et al. |
| 2002/0045263 A1 | 4/2002 | Leong et al. |
| 2002/0071843 A1 | 6/2002 | Li et al. |
| 2002/0123609 A1 | 9/2002 | Frechet et al. |
| 2002/0151004 A1 | 10/2002 | Craig |
| 2002/0156047 A1 | 10/2002 | Zhao |
| 2002/0164648 A1 | 11/2002 | Goins et al. |
| 2002/0165179 A1 | 11/2002 | Baker |
| 2002/0192843 A1 | 12/2002 | Kaganove et al. |
| 2003/0050426 A1 | 3/2003 | Shastri |
| 2003/0059461 A1 | 3/2003 | Backer et al. |
| 2003/0064050 A1 | 4/2003 | Malik et al. |
| 2003/0064984 A1 | 4/2003 | Ng et al. |
| 2003/0068379 A1 | 4/2003 | Li et al. |
| 2003/0073852 A1 | 4/2003 | Ng et al. |
| 2003/0077295 A1 | 4/2003 | Malik et al. |
| 2003/0082103 A1 | 5/2003 | Wartchow et al. |
| 2003/0083286 A1 | 5/2003 | Teng et al. |
| 2003/0129223 A1 | 7/2003 | Wartchow et al. |
| 2003/0133972 A1 | 7/2003 | Danthi et al. |
| 2003/0147812 A1 | 8/2003 | Ueberle et al. |
| 2003/0170311 A1 | 9/2003 | Russell |
| 2003/0175209 A1 | 9/2003 | Mueller et al. |
| 2003/0181619 A1 | 9/2003 | Matyjaszewski et al. |
| 2003/0190364 A1 | 10/2003 | Panitch et al. |
| 2003/0219785 A1 | 11/2003 | Hallahan et al. |
| 2003/0232929 A1 | 12/2003 | Huang et al. |
| 2003/0232968 A1 | 12/2003 | Li et al. |
| 2004/0028745 A1 | 2/2004 | Bouhadir et al. |
| 2004/0142475 A1 | 7/2004 | Barman et al. |
| 2004/0151689 A1 | 8/2004 | Majoros et al. |
| 2004/0161403 A1 | 8/2004 | Zhao et al. |
| 2004/0228831 A1 | 11/2004 | Belinka et al. |
| 2004/0247680 A1 | 12/2004 | Farokhzad et al. |
| 2005/0019923 A1 | 1/2005 | Uchegbu et al. |
| 2005/0025820 A1 | 2/2005 | Kester et al. |
| 2005/0036973 A1 | 2/2005 | Sato et al. |
| 2005/0037075 A1 | 2/2005 | Farokhzad et al. |
| 2005/0042753 A1 | 2/2005 | Yang et al. |
| 2005/0112088 A1 | 5/2005 | Zhao et al. |
| 2005/0119450 A1 | 6/2005 | Wang et al. |
| 2005/0147681 A1 | 7/2005 | Zhao |
| 2005/0147688 A1 | 7/2005 | Russell |
| 2005/0169882 A1 | 8/2005 | Lowe et al. |

\* cited by examiner

Building block  G0 (Core)

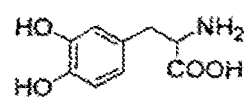
Figure 25 A
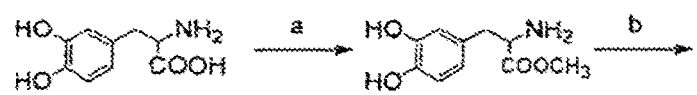
Figure 25 B
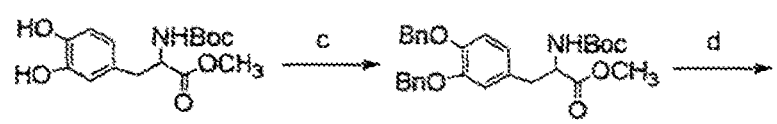
Figure 25 C            Figure 25 D
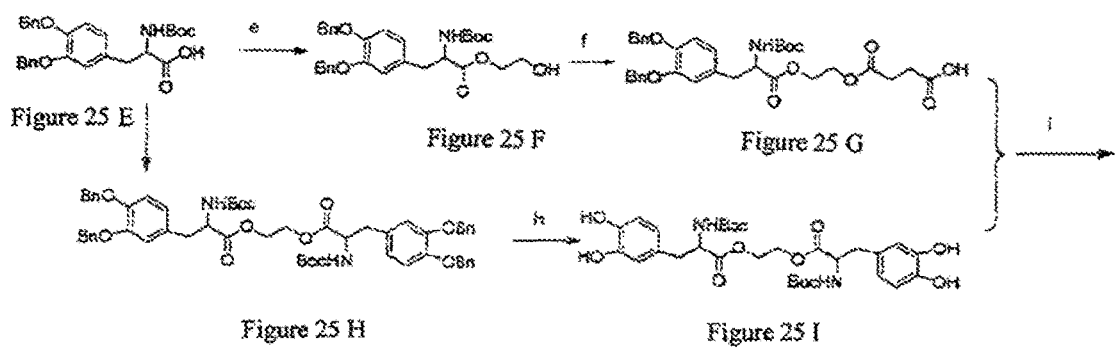
Figure 25 E
Figure 25 F            Figure 25 G
Figure 25 H            Figure 25 I

+

Compound Fig. 25H

+

Compound Fig. 25H

METHOD OF PREPARING DENDRITIC DRUGS

This application claims priority from U.S. Provisional 60/761,439 filed Jan. 24, 2006.

BACKGROUND OF THE INVENTION

This invention deals with a synthetic design of drug-incorporated novel dendrimers for quantitatively controlled drug delivery.

Dendrimers are well known in the art and there are multiple patents, treatises, and textbooks on their preparation and use.

Dendrimers have unique cascade structures with multiple functional termini. The multifunctional surface of dendrimers makes them easy to chemically conjugate with other molecules, such as drugs, for targeted delivery and controlled release of the drugs. Up to now, little attention has been paid to utilizing the cascade feature of dendrimer structures for controlled-release of drugs. This invention takes advantage of this distinct feature to develop an ideal drug delivery system since each layer of the structure can be tailored with a certain amount of drug entities that are well defined by the dendrimer structure.

Under proper physiological conditions, the dendritic drug can be degraded naturally or digested by enzymes to release the drugs sequentially and quantitatively layer by layer. The drugs on the surface, or exterior of the dendrimer, are released first, and then the interior drug units begin to be liberated when all of the periphery drug units have left. The drug units at the core of the dendrimer will be released last. Thus, a well-controlled quantitative delivery of the drug can be approached through this dendritic design.

At the current time, there are two known methods for utilizing dendrimers in drug delivery, dendrimer drug conjugation and dendrimer drug encapsulation. In the conjugation method, a drug is attached to the surface of the carrier molecule, i.e. the dendrimer, and the encapsulation method utilizes the dendritic voids to accommodate the drug molecules for improving the drug properties such as solubility and toxicity in therapeutic treatment.

However, both methods have limitations in drug controlled release and targeted delivery. For example, in the dendrimer, the conjugated drugs are only located on the surface of the dendrimer and they all can be easily released at the same time. Therefore, the drug-controlled release will be obviously limited in this system. The encapsulation of drugs with dendrimers is rather unstable for in vivo applications since the drugs are just physically entrapped inside the dendritic voids and the leakage of the drug can be a big issue during the delivery.

Examples of U.S. Patents and publications that deal with dendrimer drug encapsulation, dendrimer drug conjugation and alternative drug delivery systems are: U.S. Pat. No. 6,756,037 to Greenwald et al.; U.S. Pat. No. 6,838,528 to Zhao; U.S. Pat. No. 6,942,877 to Vogt, et al.; U.S. Pat. No. 6,913,760 to Carr, et al.; U.S. Pat. No. 6,681,068 to Ng, et al.; U.S. Pat. No. 6,576,222 to Platzek, et al.; U.S. Pat. No. 5,945,100 to Fick; U.S. Pat. No. 6,864,350 to Harris; U.S. Pat. No. 6,790,437 to Malik, et al.; U.S. Pat. No. 6,706,892 to Eziin, et al.; U.S. Pat. No. 6,623,729 to Park et al.; U.S. Pat. No. 6,475,495 to Maignan; U.S. Pat. No. 6,458,347 to Sugawara, et al.; U.S. Pat. No. 6,432,423 to Maignan; U.S. Pat. No. 6,296,842 to Jaworowicz, et al.; U.S. Pat. No. 6,623,764 to Sokoll, et al.; U.S. Pat. No. 6,623,730 to Williams, et al.; U.S. Pat. No. 6,600,010 to Mao, et al.; U.S. Pat. No. 6,280,745 to Flore, et al.; U.S. Pat. No. 5,965,119 to Greenwald, et al.; U.S. Pat. No. 6,861,066 to Van de Casteele; U.S. Patent publication 2005/0169882 A1 to Lowe, et al.; U.S. Patent publication 2005/0147688 A1 to Van de Casteele; U.S. Patent publication 2005/0147681 A1 to Zhao; U.S. Patent publication 2005/0119450 A1 to Wang, et al.; U.S. patent publication 2005/0112088 A1 to Zhao, et al.; U.S. Patent publication 2005/0042753 A1 to Yang, et al.; U.S. Patent publication 2005/0037075 A1 to Farokhzad, et al.; U.S. Patent publication 2005/0036973 A1 to Sato, et al.; U.S. publication 2005/0025820 A1 to Kester, et al.; U.S. Patent publication 2005/0019923 A1 to Uchegbu, et al.; U.S. Patent publication 2004/0247680 A1 to Farokhzad, et al.; U.S. Patent publication 2004/0228831 A1 to Belinka, et al.; U.S. Patent publication 2004/0161403 A1 to Zhao, et al.; U.S. Patent publication 2004/0151689 to Majoros, et al.; U.S. Patent publication 2004/0142475 A1 to Barman, et al.; U.S. Patent publication 2004/0028745 A1 to Bouhadir, et al.; U.S. Patent publication 2003/0232968 A1 to Li, et al.; U.S. Patent 2003/0232929 A1 to Huang, et al.; U.S. Patent publication 2003/0219785 A1 to Hallahan, et al.; U.S. Patent publication 2003/0190364 A1 to Panitch, et al.; U.S. Patent publication 2003/0181619 A1 to Matyjaszewski et al.; U.S. Patent publication 2003/0175209 A1 to Mueller, et al.; U.S. Patent publication 2003/0170311 A1 to Van de Casteele; U.S. Patent publication 2003/0147812 A1 to Ueberle; U.S. Patent publication 2003/0133972 A1 to Danthi, et al.; U.S. Patent publication 2003/0129223 A1 to Wartchow, et al.; U.S. Patent publication 2003/0083286 A1 to Teng, et al.; U.S. Patent publication 2003/0082103 A1 to Wartchow, et al.; U.S. Patent Publication 2003/0077295 A1 to Malik, et al.; U.S. Patent publication 2003/0073852 A1 to Ng, et al.; U.S. Patent publication 2003/0068379 A1 to Li, et al.; U.S. Patent publication 2003/0064984 A1 to Ng, et al.; U.S. Patent publication 2003/0064050 A1 to Malik, et al. U.S. Patent publication 2003/0059461 A1 to Backer, et al.; U.S. Patent publication 2003/0050426 A1 to Shastri; U.S. Patent publication 2002/0192843 A1 to Kaganove, et al.; U.S. Patent publication 2002/0165179 A1 to Baker; U.S. Patent publication 2002/0164648 A1 to Goins, et al.; U.S. Patent publication 2002/0156047 A1 to Zhao; U.S. Patent publication 2002/0151004 A1 to Craig; U.S. Patent publication 2002/0123609 A1 to Frechet, et al.; U.S. Patent publication 2002/0071843 A1 to Li, et al.; U.S. Patent publication 2002/0045263 A1 to Leong, et al.; U.S. Patent publication 2002/0022012 A1 to Cooper, et al.; U.S. Patent publication 2002/0000681 A1 to Gupta, et al.; U.S. Patent publication 2001/0011109 A1 to Balogh, et al., and U.S. Patent publication 2001/0007666 A1 to Hoffman, et al.

Linear polymeric drugs have been discovered for drug delivery applications. For example in U.S. Pat. No. 6,613,807, that issued on Sep. 2, 2003 and U.S. Pat. No. 6,468,519 that issued on Oct. 22, 2002, both to Uhrich, there is disclosed therapeutic polyanhydride compounds for drug delivery. Uhrich also discloses linear drugs in U.S. Pat. No. 6,689,350, that are based on therapeutic polyesters and polyamides.

The linear drugs dissociate into free drug units under certain critical conditions, leading to the sudden release of the drug. Thus, the control of the drug delivery for linear drugs is not well controlled and the drug release is not quantitative.

The dendritic drugs of this invention have better control and thus a quantitative drug release can be obtained. There is no prior art relating to drugs that control release both sequentially and quantitatively like the dendritic drugs of this invention.

BRIEF DESCRIPTION OF THE DRAWINGS

FIG. 25A is HO-DOPA-$NH_2$-COOMe.

FIG. 25B is HO-DOPA-NH-Boc-COOMe.

FIG. 25C is Benzyl-DOPA-NH-Boc-COOMe.

FIG. 25D is the preparation of HO-$G_1$-$NH_2$.

FIG. 25E is the preparation of HO-$G_2$-$NH_2$.

FIG. 25F is the preparation of HO-G3-$NH_2$.

DETAILED DESCRIPTION OF THE INVENTION

Figure 1:
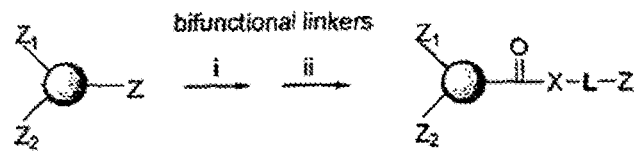
FIG. 1 is the preparation of the building block 200 starting with reacting drug 100 and bifunctional linkers.

The instant invention deals with the synthetic design of drug-incorporated novel dendrimer structures for quantitative controlled drug delivery.

With more specificity, this invention deals, in one embodiment, with a method of preparing a dendritic drug, the method comprising providing a therapeutically active multifunctional drug, wherein the drug has at least one reactive group capable of providing a linker site. The drug also has at least one functional group capable of providing a starting point for the preparation of a dendritic structure.

Any reactive group in the drug that is not capable of providing a linker site or providing a starting point for the preparation of a dendritic molecule is chemically protected. Also, before any synthetic modification, any reactive groups capable of providing a linker site and any functional group capable of providing a starting point for the preparation of a dendritic molecule are first chemically protected.

The method then provides the deprotection of the protected group formed when the original linker sites of the starting drug molecule are chemically protected, and then reacting the deprotected groups with a first linker group selected from the group consisting of biologically compatible compounds, biologically inactive compounds, biologically active compounds, biologically compatible and bioactive compounds, biologically compatible and biologically inactive compounds.

The product from the above reaction (just Supra) is reacted with a second linker group selected from the group consisting of biologically compatible compounds, biologically inactive compounds, biologically active compounds, combinations of biologically compatible and bioactive compounds, and combinations of biologically compatible and biologically inactive compounds. The product of the reaction serves as the building block for the preparation of the dendritic drug.

Next, two units of building block molecules formed during the reactions of the first linker and second groups are coupled together with a linker molecule or two linker molecules, to yield a core molecule for the preparation of the dendritic drug.

Thereafter, a predetermined amount of active sites in the core formed in the coupling reaction above are generated by deprotecting the protected linker sites of the core for the preparation of a dendritic molecule. So the core to be used for building up the dendritic drug is still chemically protected, with any groups in the drug precursor that is not capable of providing a linker site or providing a starting point for the preparation of a dendritic molecule. Then the synthesis of the first generation dendritic drug, can be done by reacting the active linker sites of the core molecule with the certain amount of building block molecules (based on number of the active sites), then deprotecting the rest of protected groups in the formed structure to give a first generation dendritic drug.

What follows is the format used in the claims so that the method can be more easily followed.

Thus, the invention deals with a method of preparing a dendritic drug, the method comprising (I) providing a therapeutically active multifunctional drug, said drug having at least one reactive group capable of providing a linker site, said drug having at least one functional group capable of providing a starting point for the preparation of a dendritic molecule; (II) chemically protecting any reactive group in the drug that is not capable of providing a linker site or providing a starting point for the preparation of a dendritic molecule; (III) chemically protecting any reactive groups capable of providing a linker site; (IV) chemically protecting any functional group capable of providing a starting point for the preparation of a dendritic molecule; (V) deprotecting any group formed in (III); (VI) reacting any group formed in (V) with a first linker group selected from the group consisting of: (i) biologically compatible compounds, (ii) biologically inactive compounds, (iii) biologically active compounds, (iv) biologically compatible and bioactive compounds, (v) biologically compatible and biologically inactive compounds; (VII) reacting the first linker from (VI) with a second linker group selected from the group consisting of (i) biologically compatible compounds, (ii) biologically inactive compounds, (iii) biologically active compounds, (iv) biologically compatible and bioactive compounds, (v) biologically compatible and biologically inactive compounds; (VIII) coupling two units formed in (VI) through the first linker groups; (IX) deprotecting the groups formed in (V) to yield a core molecule for the dendritic drug; (X) reacting a predetermined amount of the molecules formed in (VI) with each one equivalent of the molecule formed in (VII), and deprotecting the protected groups formed in (IV); deprotecting any group in the molecule that is not capable of providing a linker site or providing a starting point for the preparation of a dendritic molecule to give a first generation dendritic drug.

Another embodiment of this invention is treating the first generation dendritic drug iteratively using steps (X) and (Xl) to form higher generation dendritic drugs.

Still further, an additional embodiment of this invention is to provide a process for preparing and dendritic drugs wherein more than one type of drug is incorporated into the dendritic molecule.

An additional embodiment of this invention is a dendritic drug prepared by the processes set forth above.

Yet another embodiment of this invention is a dendritic drug that will release biologically active compounds when decomposed by the biological degenerative action of a mammalian body.

Still another embodiment of this invention is a pharmaceutical composition comprising the dendritic drug and a pharmaceutical carrier.

Another embodiment of this invention is a therapeutic method of treating a disease in an animal comprising administering to an animal an effective amount of a dendritic drug as disclosed herein.

Going to another embodiment of this invention there is a method of delivering a biologically active compound to a host comprising administering to the host, a dendritic drug as disclosed herein.

A final embodiment is a dendritic drug wherein the dendritic drug has a dendritic cascade structure wherein bioactive material in incorporated into the chemical structure of the dendritic cascade structure. The dendritic cascade structure has biocompatible linking groups that are capable of degenerating under the influence of enzymes or degenerating under the influence of the bioactivity of a host body to provide controlled release of the bioactive material.

The method of this invention uses biocompatible linkers with biodegradable bonding such that drug molecules can be incorporated into a dendritic structure to form a dendritic drug that consists of a known amount of drug molecules. Each layer of the cascade structure of the dendrimer will contain a known amount of drug units, with the largest amount at the periphery and the least amount at the core of the dendrimer.

It is believed by the inventors herein that these unique dendritic drugs by having better control over release of the drug, reduces the toxic effect from drug accumulation.

The use of biologically active compounds in this invention includes therapeutic agents that provide a therapeutically desirable effect when administered to an animal. Therapeutic agents that can be incorporated into the drugs of this invention are those that are suitably functionalized analgesics, anesthetics, anti-Parkinson's agents, anti-infectives, anti-acne agents, antibiotics, anticholinergics, anticoagulants, anticonvulsants, anti-diabetic agents, anti-dyskinetics, antifibrotic agents, antifibrotics, antifungal agents, antiglaucoma agents, anti-inflammatory agents, antineoplastics, antiosteoporotics, antipagetics, antiporatics, antipyretics, antiseptics/disinfectants, antithrombotics, bone resorption inhibitors, calcium regulators, cardioprotective agents, cardiovascular agents, central nervous system stimulants, cholinesterase inhibitors, contraceptives, deodorants, dopamine receptor agonists, erectile dysfunction agents, fertility agents, gastrointestinal agents, gout agents, hormones, hypnotics, immunomodulators, immunosuppressives, keratolytics, migraine agents, motion sickness agents muscle relaxants, nucleoside analogs, obesity agents, ophthalmic agents. Osteoporosis agents, parasympatholytics, parasympathomimetics, prostaglandins, psychotherapeutic agents, respiratory agents, sclerosing agents, sedatives, skin and mucous membrane agents, smoking cessation agents, sympatholytics, synthetic antibacterial agents, ultraviolet screening agents, urinary tract agents, vaginal agents, and vasodilators (see Physicians' Desk Reference, 55 ed., 2001, Medical Economics Company, Inc., Montvale, N.J., pages 201 to 202).

Suitable examples of drugs with the required functional groups within their structure can be found in almost all classes of drugs including, but not limited to, analgesics, anesthetics, anti-acne agents, antibiotics, synthetic antibacterial agents, anticholinergics, anticoagulants, anti-dyskinetics, antifibrotics, antifungal agents, antiglaucoma agents, anti-inflammatory agents, antineoplastics, antiosteoporotics, antipagetics, anti-Parkinson's agents, antisporatics, antipyretics, antiseptics/disinfectants, antithrombotics, bone resorption inhibitors, calcium regulators, keratolytics, sclerosing agents and ultraviolet screening agents.

Lists of therapeutic agents can be found, for example, in the Physicians' Desk Reference, referred-to Supra, USPN Dictionary of USAN and International Drug Names, 2000, The United States Pharmacopoeia Convention, Inc., Rockville, Md.; and the Merck Index, 12 ed., 1996, Merck & Co., Inc., Whitehouse Station, N.J. One skilled in the art can readily select therapeutic agents that possess the necessary functional groups for use in this invention.

Examples of anti-bacterial compounds suitable for use in the present invention include, but are not limited to, 4-sulfanilamidosalicylic acid, acediasulfone, amfenac, amoxicillin, ampicillin, apalcillin, apicycline, asosicillin, axtreonam, bambermycins, biapenem, carbenicillin, carumonam, cefadroxil, cefamandole, cefatrizine, cefbuperazone, cefclidin, cefdinir, cefditoren, cefepime, cefetament, cefixime, cefinenoxime, cefininox, cefodizime, cefonicid, cefoperazone, ceforanide, cefotaxime, cefoetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, cyclacillin, enoxacin, epicillin, flomoxef, grepafloxacin, hetacillin, imipenem, lomefloxacin, lymecycline, meropenem, moxalactam, mupirocin, nadifloxacin, norfloxacin, panipenem, pazufloxacin, penicillin N, pipemidic acid, quinacillin, ritipenem, salazosulfadimidine, sparfloxacin, succisulfone, sulfachrysoidine, sulfaloxic acid, teicoplanin, temafloxacin, temocillin, ticarcillin, tigemonam, tosulfoxacin, trovafloxacin, vancomycin, and the like.

Examples of anti-fungal compounds suitable for use in the present invention include, but are not limited to, amphotericin B, azaserine, candicidins, lucensomycin, natamycin, nystatin, and the like.

Examples of anti-neoplastic compounds suitable for use in the instant invention include, but are not limited to, 6-diazo-5-oxo-L-norleucine, azaserine, carzinophillin A, denopterin, edatrexate, eflomithine, melphalan, methotrexate, mycophenolic acid, podophyllinic acid 2-ethylhydrizide, pteropterin, streptonigrin, Tomudex® (N-((5-(((1,4-Dihydro-2-methyl-4-oxo-6-quinazolinyl)methyl)methyl-amino)-2-thienyl)carbonyl)-L-glutamic acid), ubenimex, and the like.

Examples of anti-thrombics useful in the instant invention include, but are not limited to, argatroban, iloprost, lamifiban, taprostene, tirofiban and the like.

Examples of immunosuppressive compounds suitable for use in the present invention include, but are not limited to, bucillamine, mycophenolic acid, proceodazole, romurtide, ubenimex and the like.

Examples of NSAID compounds suitable for use in the instant invention include, but are not limited to 3-amino-4-hydroxybutyric acid, aceclofenac, alminoprofen, bromfenac, bumadizon, carprofen, diclofenac, diflunisal, enfenamic acid, etodolac, fendosal, flufenamic acid, gentisic acid, meclofenamic acid, mefenamic acid, mesalamine, niflumic acid, olsalazine oxaceprol, S-adenosylmethionine, salicylic acid, salsalate, sulfasalizine, tolfenamic acid, and the like.

The dendritic drugs prepared by the method of the instant invention can be used neat, or can be formulated as pharmaceutical compositions and administered to a mammalian host, such as a human patient or an animal such as a dog or horse. This can be done in a variety of forms, such as, for example, orally, rectally, or parenterally, by intravenous, intramuscular, intraperitoneal, intraspinal, intracranial, topical, ocular, and subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients or adjuvants used in the form of ingestible tablets, buccal tablets, troches, capsules, elirirs, suspensions, syrups, wafers, and the like. Such compositions and preparations preferably contain at least 0.1% by weight of the dendritic drug. The percentage of the compositions and preparations may be varied and may conveniently be between about 0.1% to about 100% by weight of the composition as long as an effective dosage level is maintained.

The tablets, troches, pills, capsules, and the like may also contain the following. Binders, such as gum tragacanth, acacia, corn starch or gelatin, excipients such as dicalcium phosphate, a disintegrating agent such as corn starch, potato starch, alginic acid and the like, a lubricant such as magnesium stearate, and a sweetening agent such as sucrose, fructose, lactose, or aspartame or a flavoring agent such as peppermint, oil of wintergreen, or cherry flavoring.

When the unit dosage form is a capsule, it may contain, in addition to materials of the above type, a liquid carrier, such as a vegetable oil or a polyethylene glycol. Various other materials may be present as coating or to otherwise modify the physical form of the solid unit dosage form, as long as the effectiveness of the drug is not compromised. For example, tablets, pills, or capsules may be coated with gelatin, wax, shellac or sugar and the like. A syrup or elixir may contain the active compound, sucrose or fructose as a sweetening agent, methyl and propyl parabens as preservatives, a dye, and flavoring, such as cherry or orange flavor. Any material used in preparing any unit dosage form should be pharmaceutically acceptable and substantially non-toxic in the amounts employed. In addition, the active compound may be incorporated into sustained release preparations and devices.

Solutions of the dendritic drug can be prepared in a suitable solvent such as an alcohol, or mixed with a nontoxic surfactant. Dispersions can also be prepared in glycerol, liquid polyethylene glycols, triacetin, and mixtures thereof, and in certain oils, with care being taken to avoid hydrolysis of the dendritic drug. Under ordinary conditions of storage and use, these preparations can contain a preservative to prevent the growth of microorganisms.

Suitable injection or infusion forms can include sterile solutions or dispersions or sterile powders comprising the dendritic drug that are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, ethanol, a polyol, for example, glycerol, propylene glycol, liquid polyethylene glycols, and the like, vegetable oils, nontoxic glycerol esters and suitable mixtures thereof The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the dendritic drug in the required amount in the appropriate solvent with various of the other ingredients enumerated Supra, as required, followed by filter sterilization, In the case of sterile powders for the preparation of sterile injectable solutions, the preferred methods of preparation are vacuum drying and the freeze drying techniques, that yield a powder of the active ingredient plus any additional desired ingredients present in the previously sterile filtered solutions.

For topical administration, the inventive dendritic drugs can be applied in pure form. However, it will generally be desirable to administer them as compositions or formulations, in combination with a dermatologically acceptable carrier, that may be a solid or a liquid.

Useful solid carriers include finely divided solids such as talc clay, micro-crystalline cellulose, silica, alumina and the like. Useful liquid carriers include alcohols or glycols or alcohol/glycol blends, in which the present compound can be dissolved or dispersed at effective levels, optionally with the aid of non-toxic surfactants. Adjuvants such as fragrances and additional antimicrobial agents can be added to optimize the properties for a given use. The resultant liquid composition can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols modified celluloses or modified mineral materials can also be employed with liquid carriers to form spreadable pastes, gels, ointments, soaps, and the like, for application directly to the skin of the user.

Examples of useful dermatological compositions that can be used to deliver the dendritic drugs of this invention to the skin are known in the art, for example, Jacquet et al in U.S. Pat. No. 4,608,392; Geria in U.S. Pat. No. 4,992,478, Smith et al in U.S. Pat. No. 4,559,157 and Wortzman, in U.S. Pat. No. 4,820,508.

Useful dosages of the drugs can be determined by comparing their in vitro activity, and in vivo activity of the therapeutic agent in animal modes. Methods for the extrapolation of effective dosages in mice, and other animals, to humans are known in the art, for example, (see U.S. Pat. No. 4,938,949). Additionally, useful dosages can be determined by measuring the rate of hydrolysis for a given drug under various physiological conditions. The amount of the drug required for use in treatment will vary not only with the particular polymer selected, but also with the route of administration, the nature of the condition being treated and the age and condition of the patient and will be ultimately at the discretion of the attendant physician or clinician.

The desired dose may conveniently be presented in a single dose or sub-divided doses administered at appropriate intervals.

The dendritic drugs of the instant invention are also useful for administering a combination of therapeutic agents to an animal. Such a combination therapy can be carried out in the following ways: 1) a second therapeutic agent can be dispersed within the polymer matrix of the dendritic structure of the dendritic drug of this invention which can be released upon degradation of the drug; 2) a second therapeutic agent can be appended to the dendritic drug, that is, not in the backbone of the polymer with bonds that hydrolyze to release the second therapeutic agent under physiological conditions; 3) the dendritic drug of this invention can incorporate two therapeutic agents into the dendritic structure, that is, a dendritic drug that is prepared using two different types of drugs and, 4) two dendritic drugs of this invention each with a different therapeutic agent can be administered together or within a short time of each other.

As will abundantly clear to one skilled in the art, suitable protecting groups can be used during the reactions illustrated herein. For example, functional groups present in the biologically active compound or the linker precursors can be protected during subsequent reactions and then the protecting groups can subsequently be removed (deprotected) to provide the eventual dendritic drugs of this invention. Some suitable protecting groups and methods for their incorporation and removal are well known in the art (see for example, Green, T. W., Wutz, P. G. M., "Protecting Groups in Organic Synthesis", second edition, 1991, New York, John Wiley & Sons, Inc.

For purposes of this invention, what is meant by "therapeutically active multifunctional drug" is any therapeutically active material that has at least one reactive functional group attached to it to provide a linker site and at least one functional group capable of providing a starting point for the preparation of a dendritic molecule of this invention. Preferred for this invention are drugs having one or two functional groups capable of providing a starting point for the preparation of the dendritic molecule. Further preferred are multifunctional drugs that have bi-functionality or tri-functionality, but the invention is not limited to those functionalities. What is meant by "chemically protecting any reactive group in the drug that is not capable of providing a linker site or providing a starting point for the preparation of a dendritic molecule" is that those groups in the therapeutically active material that are susceptible to reaction and that are part of the generic make up of the drug per se, are protected before the preparation of the dendritic drug has begun. This is to avoid undesired reactions. It is also an attempt to retain the necessary groups of the drug that make it effective as a drug.

Then, those groups that will be used to provide the linker sites are chemically protected, and then, those groups capable of providing a starting point for the preparation of a dendritic molecule are chemically protected.

The beginning of the actual construction of the dendritic drug begins with deprotecting those groups that have been chemically protected and are capable of providing a linker. Once these sites are deprotected, they can be reacted with the biologically compatible first linker groups that will eventually form the drug. For example, the linker molecule should be bi-functional for trifunctional drugs, and tri-functional for bi-functional drugs. This concept can be better understood by referring to the synthetic schemes set for a FIG. 3.

The first linker groups are then reacted with a second linker group that is also biologically compatible with the mammalian body, and then the two linker groups are reacted together. At this point in the method, the groups that are chemically protected and deprotected to form a core molecule for the dendritic drug. This part of the method provides a building block molecule that will be repeatedly used in the later steps toward the final synthesis of the dendritic drug.

The coupled units are then reacted with the groups formed from the first linker group in a ratio such that the building block molecules formed in the previous steps are reacted through their available functional groups with each one equivalent of the core molecule in a stoichiometrical amount.

Finally, deprotection is carried out until the functional groups on the original drug are available to carry out the original drug function.

What is meant herein by "bioactive material is incorporated into the chemical structure of the dendritic cascade structure" is that the bioactive materials actually form part of the structure of the dendritic cascade as opposed to being chemically reacted to the exterior surface of the dendrimer molecule (i.e. conjugated dendrimers), or being physically held in the voids of the dendrimer structure.

The reaction schematics are described infra to illustrate the invention methods.

Turning now to FIG. 1, there is shown the preparation of the building block starting with bifunctional linkers. Thus, there is shown the drug 100, having functional groups Z, $Z_1$, and $Z_2$, wherein Each of $Z_1$ and $Z_2$ are selected from the group consisting of —OH, —SH, and —$NH_2$ and Z is —COOH. The biofunctional linkers are shown as (i) and (ii) and (i) is selected from a group consisting of —OH, —SH, and —$NH_2$, while (ii) is —COOH. These reactions result in ester, thioester and amide linkages to form the building block 200 shown in FIG. 1. The various constituents are summarized in Table I, infra.

TABLE I

| Functional Group On Drug | | Functional Group On Biofunctional Linkers | | Resulting Linkage |
|---|---|---|---|---|
| $z_1$ or $z_2$ | z | i | ii | in Dendritic Drug |
| —OH | —COOH | —OH | —COOH | Ester |
| —SH | —COOH | —SH | —COOH | Thioester |
| —$NH_2$ | —COOH | —$NH_2$ | —COOH | Amide |

X in FIG. 1 is selected from the group consisting of —O—, —S—, and —NH— and L is —R'—X—CO—$(CH_2)_m$— wherein m has a value of from 2 to 20, R' is —(CHR—$CH_2)_p$—, wherein R is hydrogen or an alkyl group, and p has a value of from 1 to 10.

Figure 2:
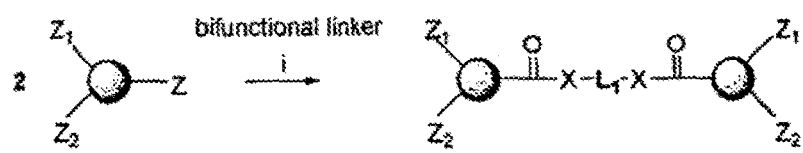
FIG. 2 is the reaction of the drug 100 using the bifunctional linker (i) to give the core ($G_0$) 300.

Turning to FIG. 2, there is shown the reaction of the drug 100 using the bifunctional linker (i) to give the core ($G_0$) 300 and in the formulae X is —O—, —S—, or —NH—; $L_1$ is —$(CH_2)_q$— wherein q has a value of from 2 to 20.

Figure 3:
FIG. 3 shows using drug 100 and bifunctional linkers (i) and (ii) to form the core ($G_0$) 400.

In the alternative, using drug 100 and bifunctional linkers (i) and (ii), the core ($G_0$) 400 can be formed as shown in FIG. 3, wherein X is —O—, —S—, or —NH—; $L_1$ is R'—X—CO—$(CH_2)_r$—CO—X—R'—, wherein r has a value of from 2 to 20, R' is —(CHR—$CH_2)_s$—, R is hydrogen or an alkyl group and s has a value of from 1 to 10.

Figure 4:
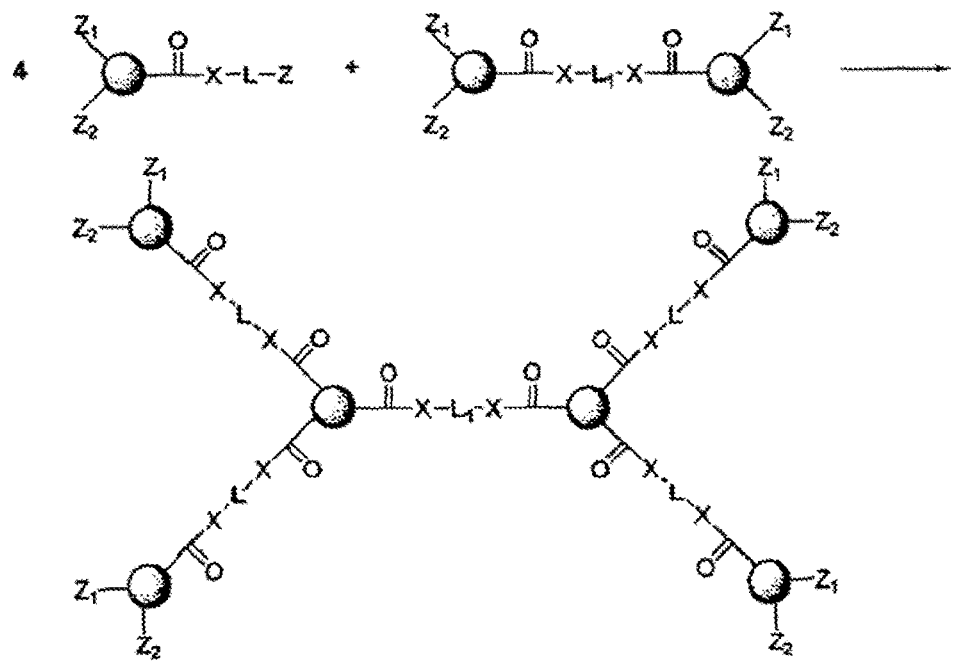
FIG. 4 is building block 200 and core 300 or 400 reacted together to form generation 1, 500.
Figure 5:
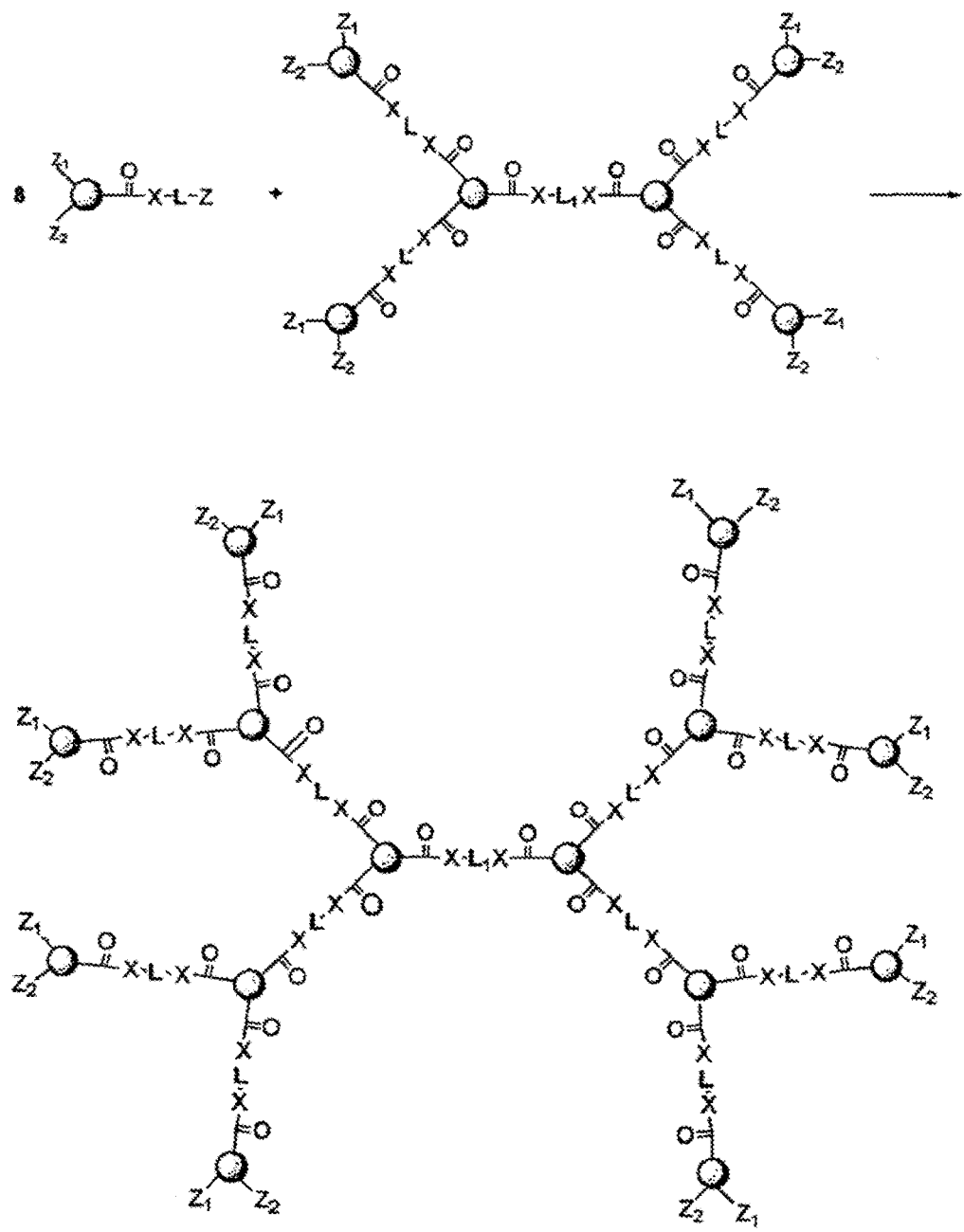
FIG. 5 is the preparation of Generation 2 (G2) 600 by using the building block 200 and the Generation 1 molecule 500.

Thereafter, building block 200 and core 300 or 400 are reacted together to form generation 1 (500) as shown in FIG. 4. Thereafter, there is shown in FIG. 5, the preparation of Generation 2 (G2) 600 by using the building block 200 and the Generation 1 molecule 500.

Figure 6:
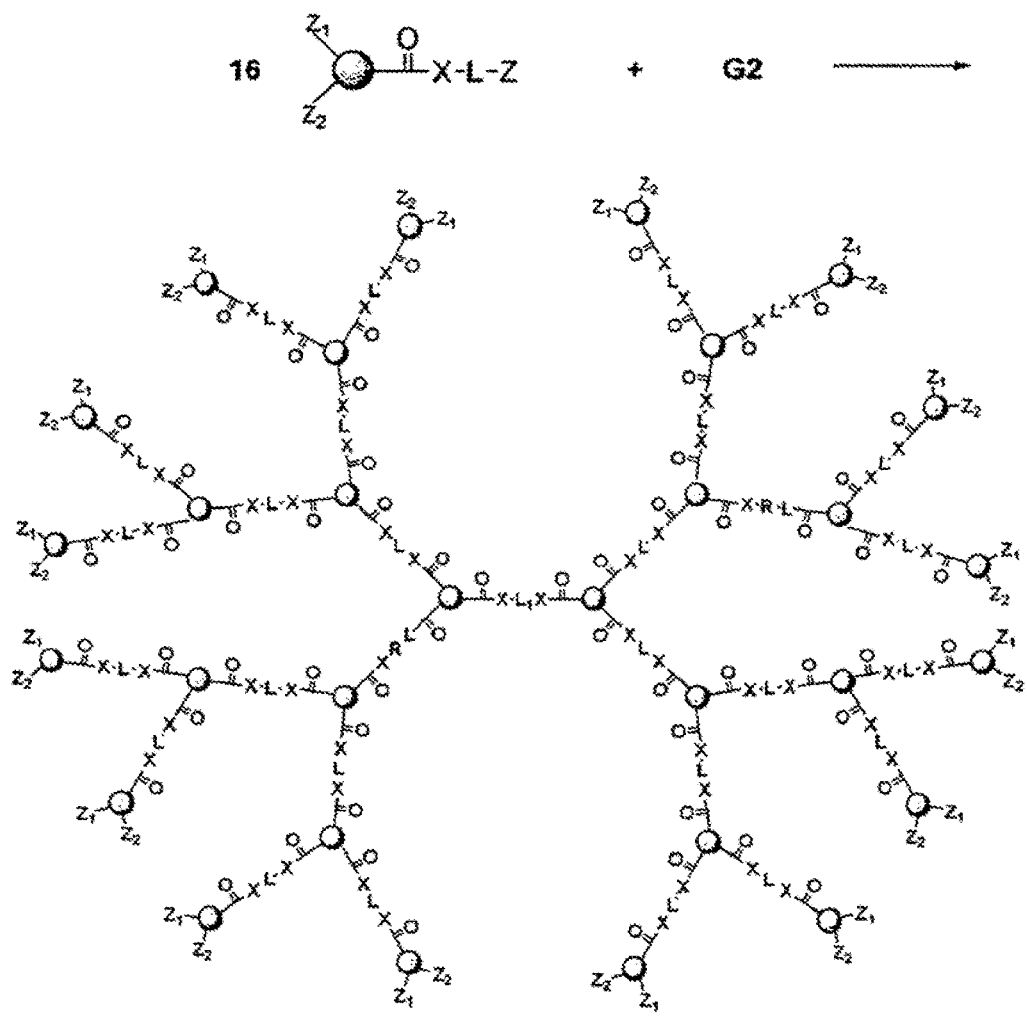
FIG. 6 is the preparation of a Generation 3 (G3) molecule 700 using building block 200 and the Generation 2 molecule 600.

The preparation of a Generation 3 (G3) molecule 700 is shown in FIG. 6 using building block 200 and the Generation 2 molecule 600.

Similarly, even higher generation dendritic drugs can be synthesized. This synthetic scheme is not limited to the use of drugs with three functionalities. Extra functional groups of the drug can be protected and finally deprotected to restore it to its intrinsic form using proper methods.

Figure 7:
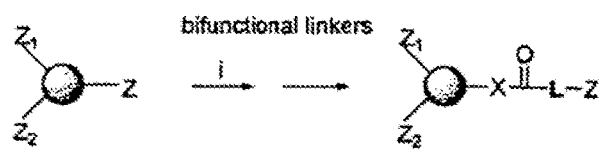
FIG. 7 is the reaction of the drug 1000 to give the building block 1100.

In a second scheme, there is shown in FIG. 7, the reaction of the drug 1000 and building block 1100, wherein $Z_1$ and $Z_2$ each are COOH, Z is selected from the group consisting of —OH, —SH, and —$NH_2$, the bifunctional linker (i) is COOH and (ii) is selected from a group consisting of —OH, —SH, —$NH_2$; X is —O—, —S—, or —NH—; L is —($CH_2$X—CO—X—R'—, wherein t has a value of from 2 to 20, R' is —(CHR—$CH_2)_u$—, R is either hydrogen or an alkyl group, and u has a value of from 1 to 10. The various constituents are summarized on Table II.

TABLE II

| Functional Group On Drug | | Functional Group On Biofunctional Linkers | | Resulting Linkage |
|---|---|---|---|---|
| $z_1$ or $z_2$ | z | i | ii | in Dendritic Drug |
| —COOH | —OH | —COOH | —OH | Ester |
| —COOH | —SH | —COOH | —SH | Thioester |
| —COOH | —$NH_2$ | —COOH | —$NH_2$ | Amide |

Figure 8:
FIG. 8 is the preparation of the core group $G_0$ 1200 using the drug 1000 and a bifunctional linker (i).
Figure 9:
FIG. 9 is the reaction of the drug 1000 and the use of bifunctional linkers (i) and (ii) to form the core 1300.

In FIG. 8, there is shown the preparation of the core group $G_0$ 1200 using the drug 1000 and a bifunctional linker (i), wherein X is —O—, —S—, or —NH— and $L_1$ is —$(CH_2)$, wherein v has a value of from 2 to 20, and in FIG. 9, there is shown the reaction scheme of the drug 1000 and the use of bifunctional linkers (i) and (ii) to form the core 1300, wherein (i) is set forth just Supra, and (ii) is selected from the group consisting of —OH, —S—, and —$NH_2$, and wherein X is —O—, —S— or —NH—; $L_1$ is —$(CH_2)_w$—COX—R'—X—CO—$(CH_2)_w$—, wherein w has a value of from 2 to 20, R' is —CHR—$CH_2)_z$—, R is hydrogen or an alkyl group, and z has a value of from 1 to 10.

Figure 10:
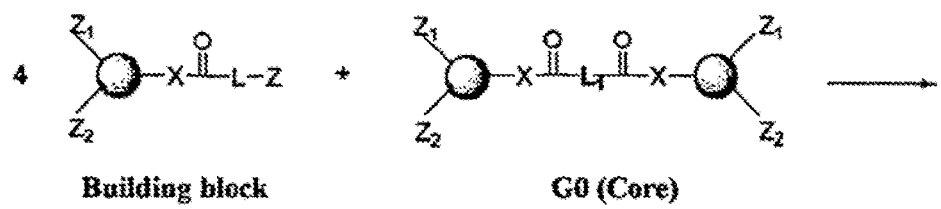
FIG. 10 illustrates the preparation of the first generation molecule 1400 using the building block 1100 and the $G_0$ core 1200 or 1300.
Figure 10:
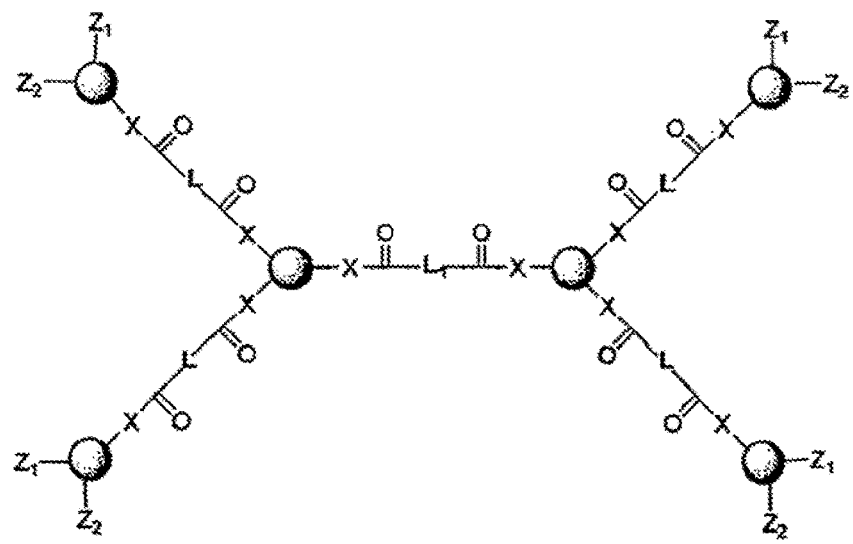
Figure 11:
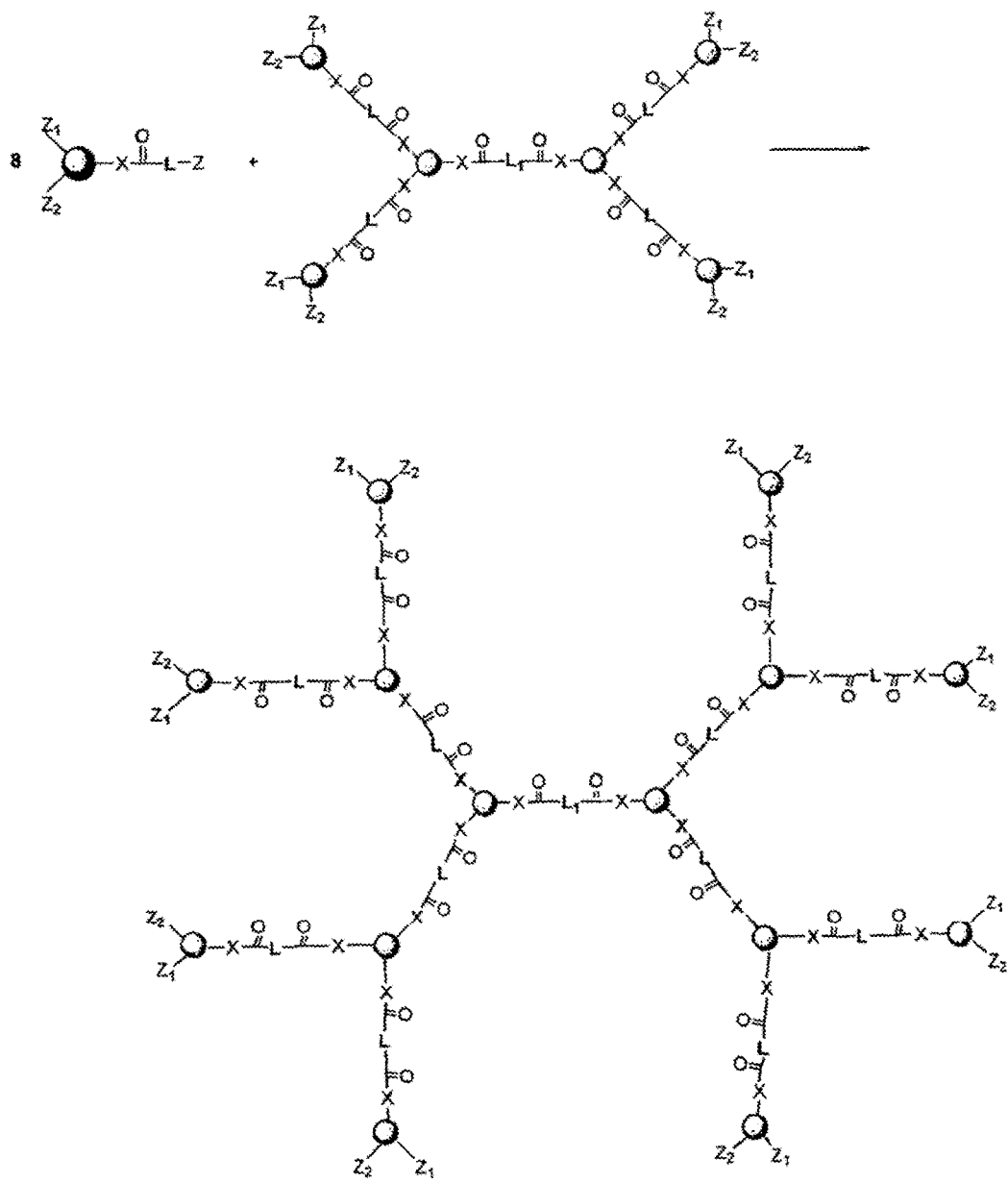
FIG. 11 shows in schematic form, the preparation of Generation 2, 1500.
Figure 12:
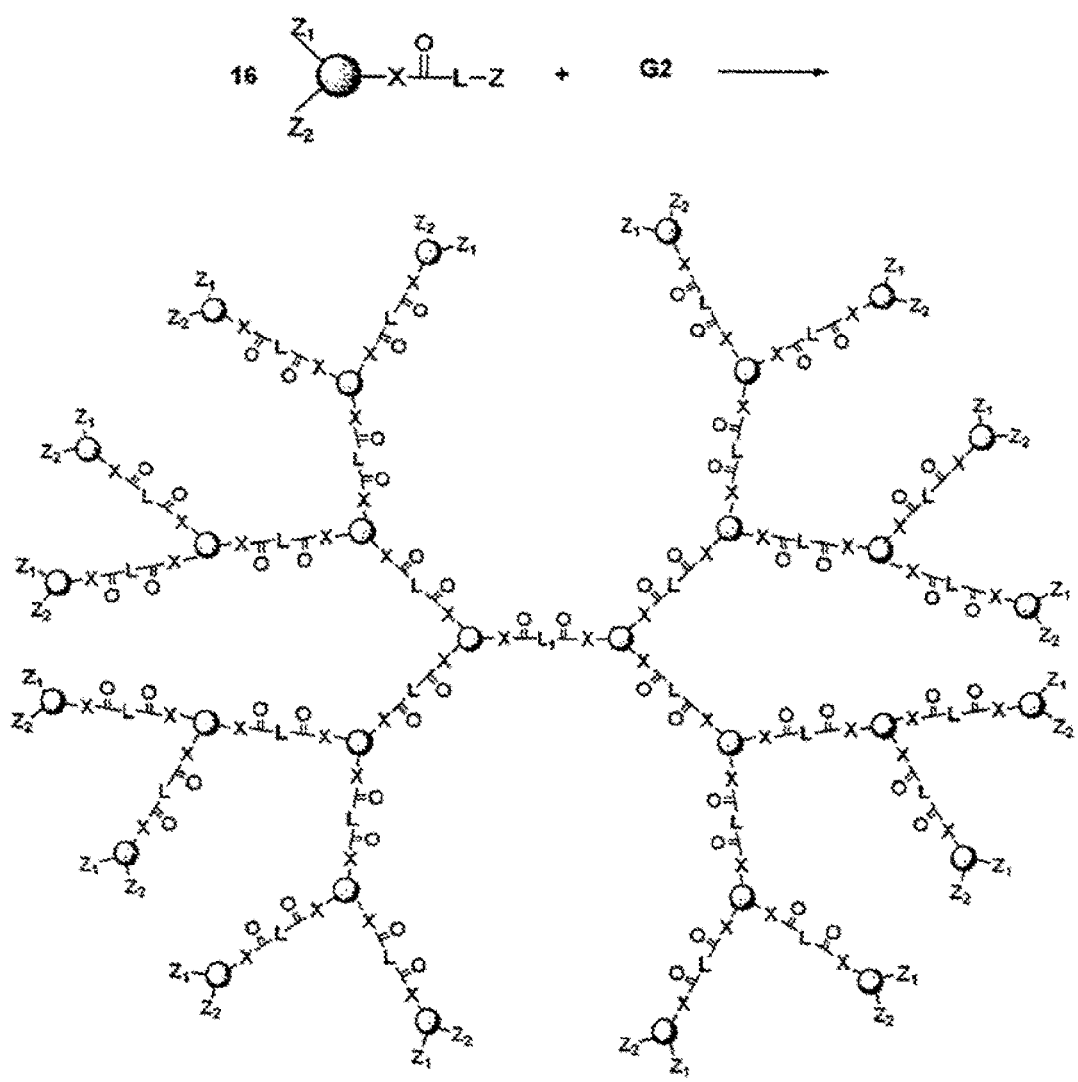
FIG. 12 shows the preparation of Generation 3 1600 dendritic drugs.

FIG. 10 illustrates the preparation of the first generation molecule 1400 using the building block 1100 and the $G_0$ core 1200 or 1300. FIG. 11 shows in schematic form, the preparation of Generation 2 1500 and FIG. 12 shows the preparation of Generation 3 1600 dendritic drugs. The various constituents are summarized on Table III.

TABLE III

| Functional Group On Drug | | Functional Group On Biofunctional Linkers | | | Resulting Linkage |
|---|---|---|---|---|---|
| $Z_1$ | $Z_2$ | Y | $Y_1$ | $Y_2$ | in Dendritic Drug |
| —OH | —COOH | —OH | —OH | —COOH | Ester |
| —SH | —COOH | —SH | —SH | —COOH | Thioester |
| —NH$_2$ | —COOH | —NH$_2$ | —NH$_2$ | —COOH | Amide |

This invention, as mentioned Supra, deals with methods using a bifunctional drug as a precursor, and the following schematics illustrate such methods.

Figure 13:
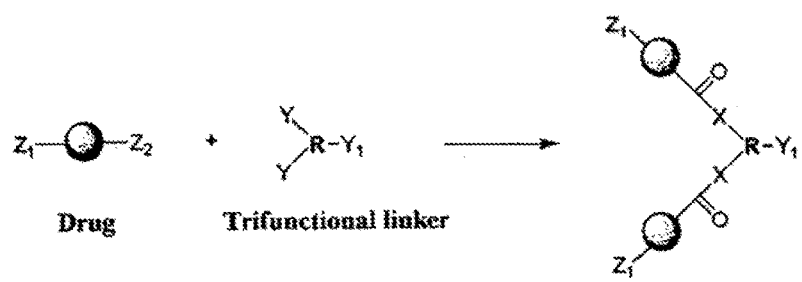
FIG. 13 is the reaction of a bifunctional drug 2000 with a trifunctional linker 2100 to give compound 2200.
Figure 14:
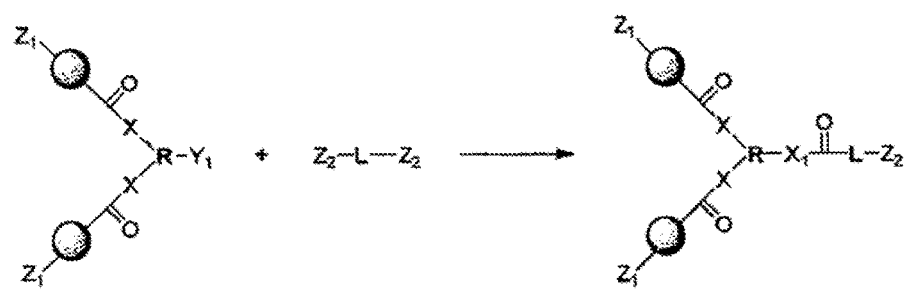
FIG. 14 shows compound 2200 reacted with a bifunctional linker 2300 to give the building block 2400
Figure 15:
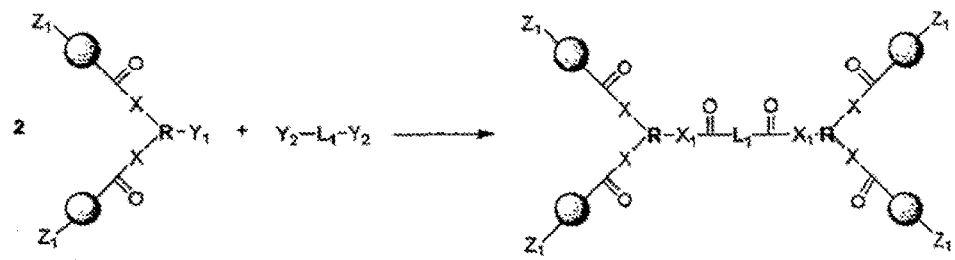
FIG. 15 shows compound 2200 reacted with a bifunctional linker 2500 to give the core molecule ($G_0$) 2600.
Figure 16:
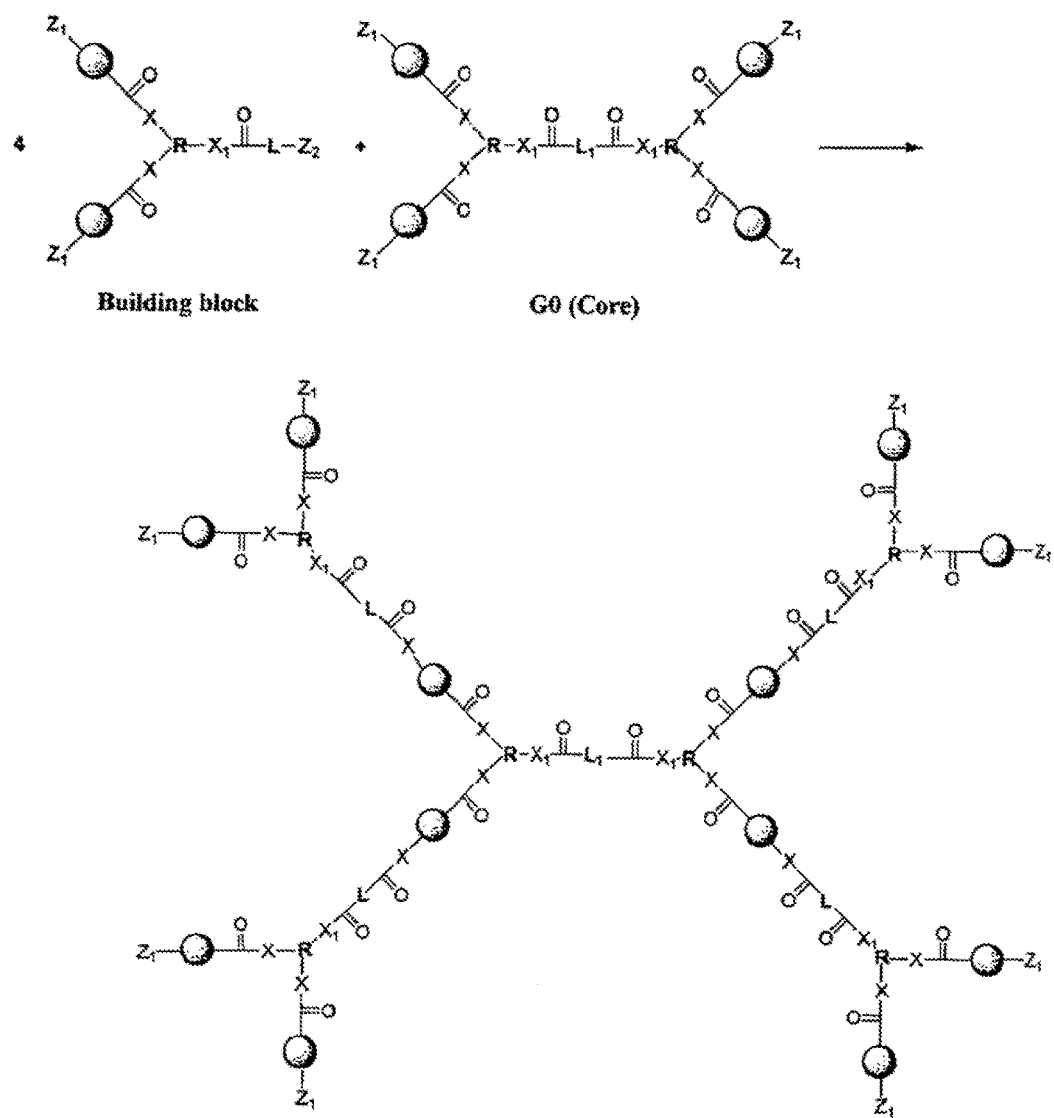
FIG. 16 shows the reaction of building block 2400 and $G_0$ 2600 to prepare Generation 1 dendritic drug ($G_1$) 2700.

Turning now to FIG. 13, there is shown the reaction of a bifunctional drug 2000 wherein $Z_1$ is selected from —OH, —SH—, and —NH$_2$— and $Z_2$ is —COOH, and a trifunctional linker group 2100 wherein Y and Yi are —OH, —SH, and —NH$_2$ to give the compound 2200. The compound 2200 is then reacted with a bifunctional linker group 2300 to give the building block 2400 as shown in FIG. 14, wherein X and $X_1$ are selected from —O—, —S—, or —NH—, and L is —(CH$_2$)$_a$—, wherein a has a value of from 2 to 20. Compound 2200 is then reacted with compound 2500 to give the core group (G$_0$) 2600 as shown in FIG. 15, wherein $Y_2$ is —COOH, $X_1$ is —O—, —S—, or —NH—, and $L_1$ is —(CH$_2$)$_b$—, wherein b has a value of from 2 to 20. Building block 2400 and G$_0$ and then reacted to give the first generation G$_1$ 2700 as shown in FIG. 16.

Figure 17:
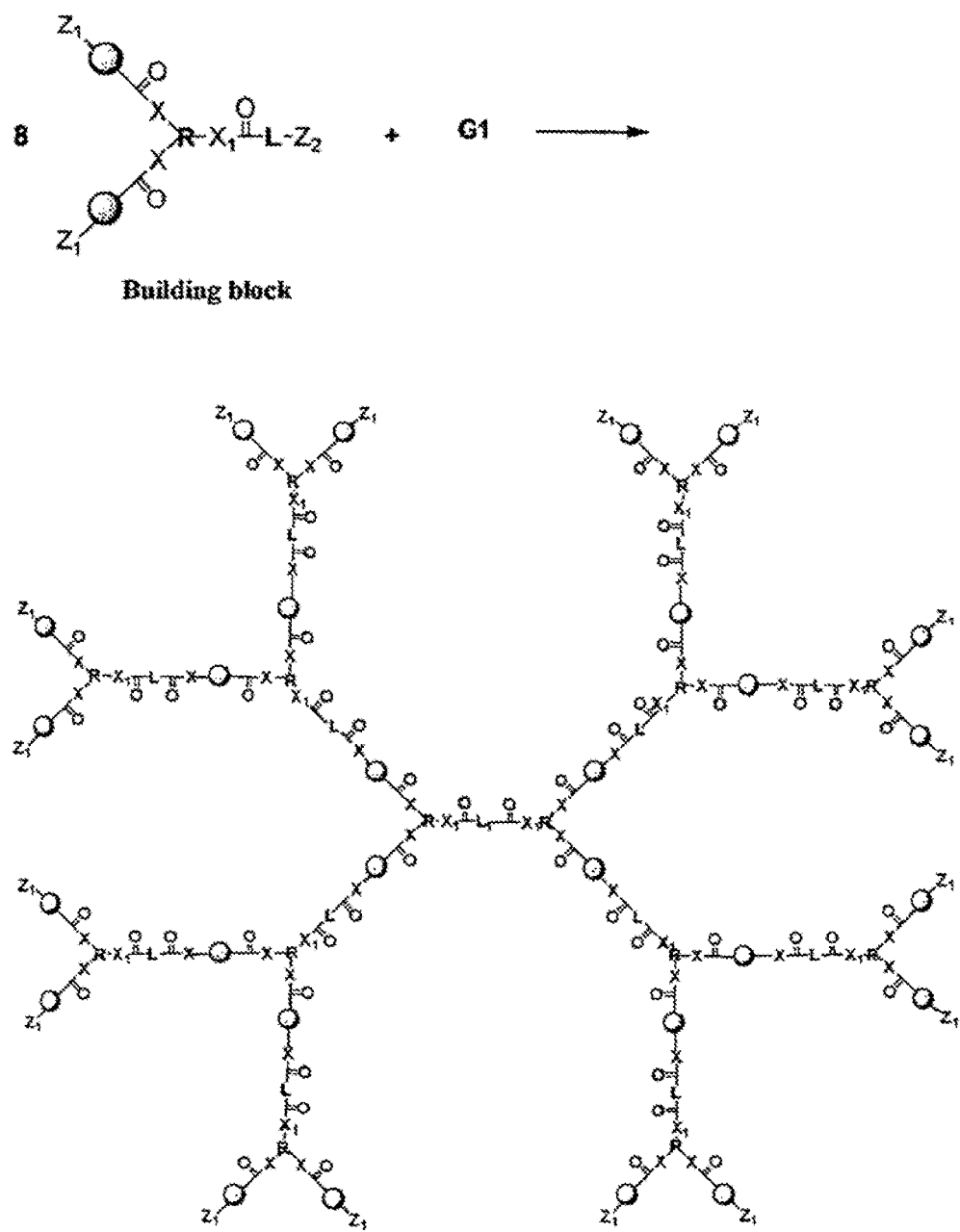
FIG. 17 shows the preparation of the second generation dendritic drug wherein building block 2400 is reacted with $G_1$ to provide Generation 2 ($G_2$) dendritic drug 2800.
Figure 18:
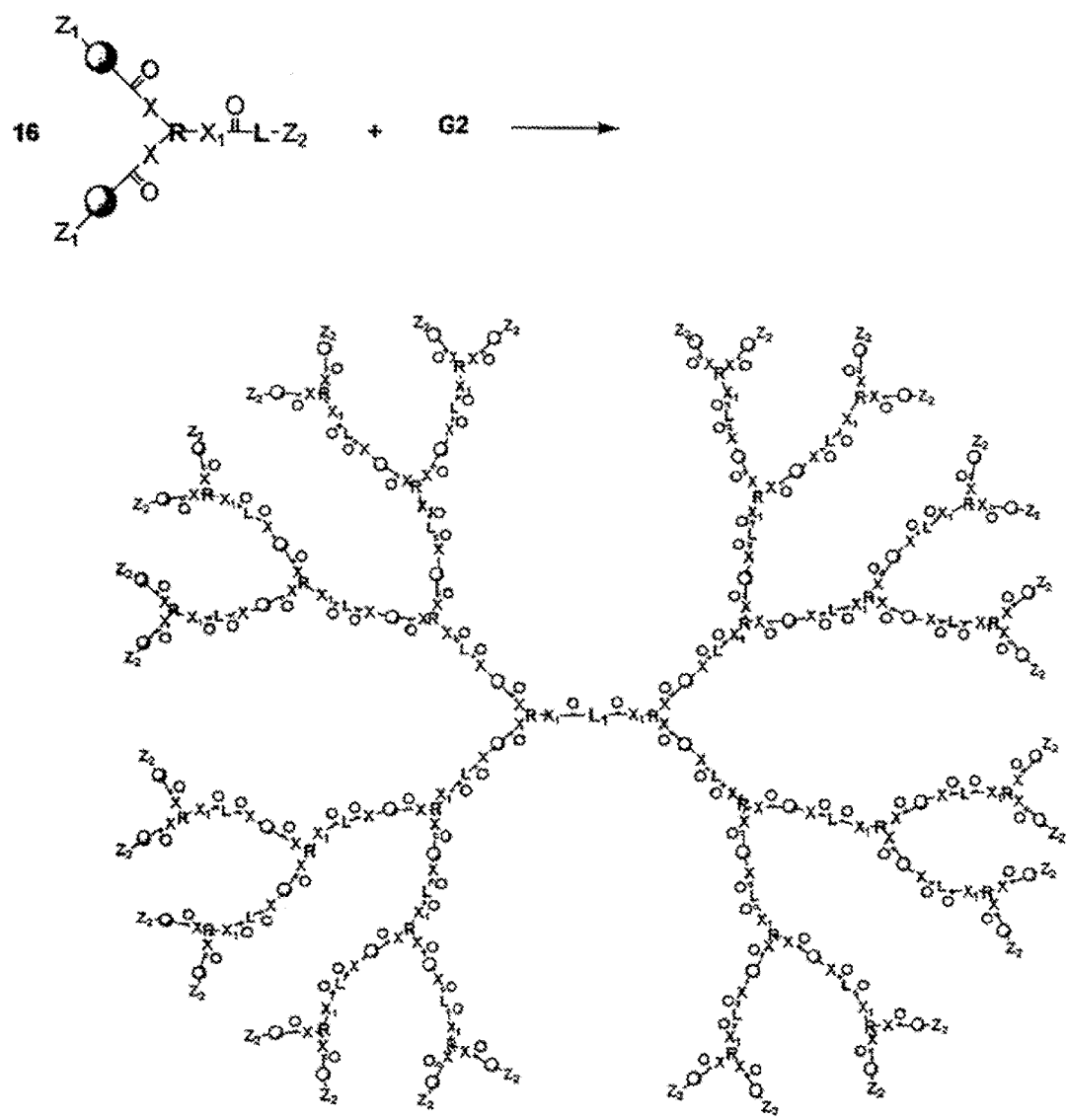
FIG. 18 shows the preparation of the third generation dendritic drug wherein building block 2400 is reacted with $G_2$ 2800 to give Generation 3 ($G_3$) dendritic drug 2900.

The second and third generations are shown in FIGS. 17 and 18, respectively, wherein building block 2400 is reacted with G$_1$ 2700 to provide G$_2$ 2800, and the building block 2400 is reacted with compound G$_2$ 2800 to give G$_3$, compound 2900. The various constituents are summarized in Table III.

TABLE IV

| Functional Group On Drug | | Functional Group On Biofunctional Linkers | | | Resulting Linkage |
|---|---|---|---|---|---|
| $Z_1$ | $Z_2$ | Y | $Y_1$ | $Y_3$ | in Dendritic Drug |
| —OH | —COOH | —OH | —OH | —OH | Ester |
| —SH | —COOH | —SH | —SH | —SH | Thioester |
| —NH$_2$ | —COOH | —NH$_2$ | —NH$_2$ | —NH$_2$ | Amide |

Figure 19:
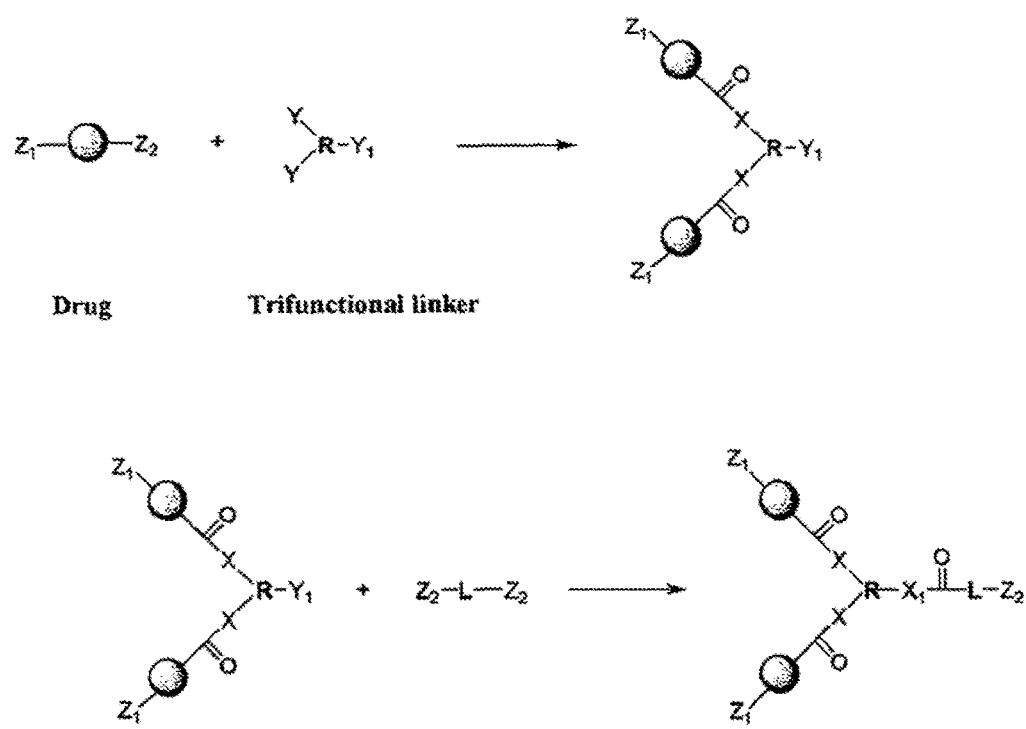
FIG. 19 shows the reaction of a bifunctional drug 2000 with a trifunctional linker 2100 to give the compound 2200 and the reaction of compound 2200 with the bifunctional linker 2300 to give the building block 2400.
Figure 20:
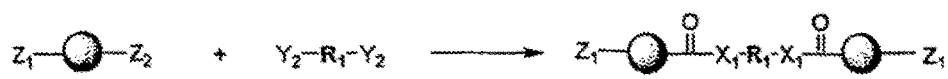
FIG. 20 shows the reaction of the drug 2000 with the bifunctional linker 3100 to give a new core molecule $G_0$, 3200.

Turning now to FIG. 19, there is shown the reaction of a bifunctional drug 2000 with a trifunctional linker 2100 to give the compound 2200 and the reaction of compound 2200 with the bifunctional linker 2300 to give the building block 2400, wherein X and $X_1$ are selected from —O—, —S—, or —NH—, and L is —(CH$_2$)$_c$—, wherein c has a value of from 2 to 20. Further, FIG. 20 shows the reaction of the drug 2000 with the bifunctional linker 3100 to give a new core molecule G$_0$, 3200.

Figure 21:
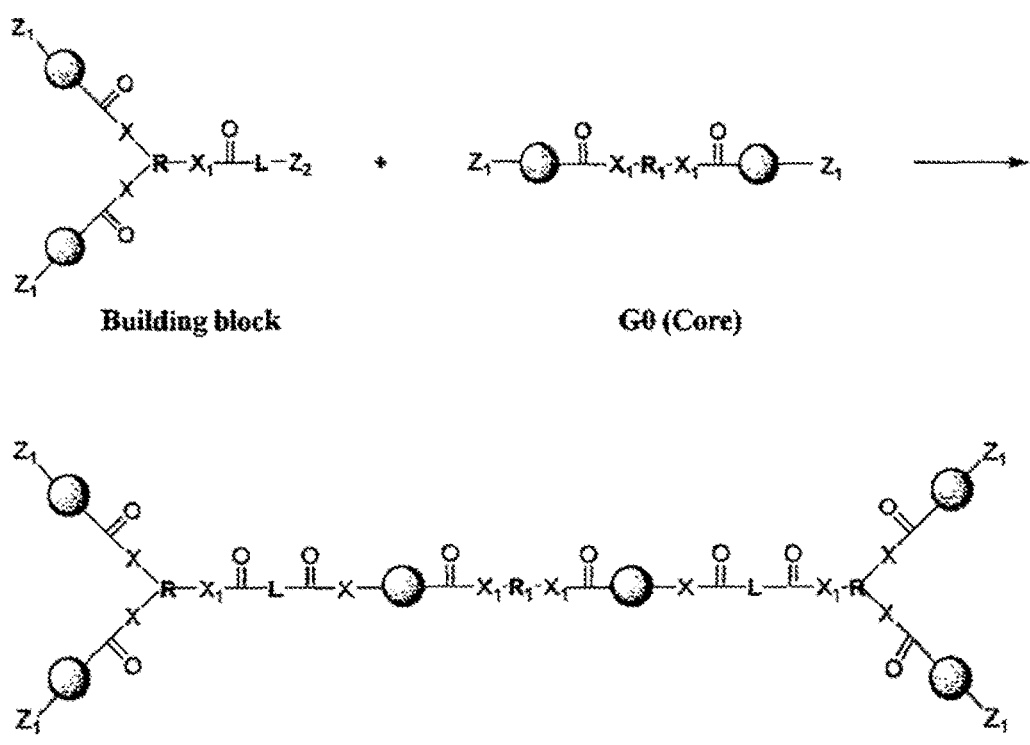
FIG. 21 shows the building block 2400 reacted with the new core 3200 to give the first generation dendritic drug ($G_1$) 3300.
Figure 22:
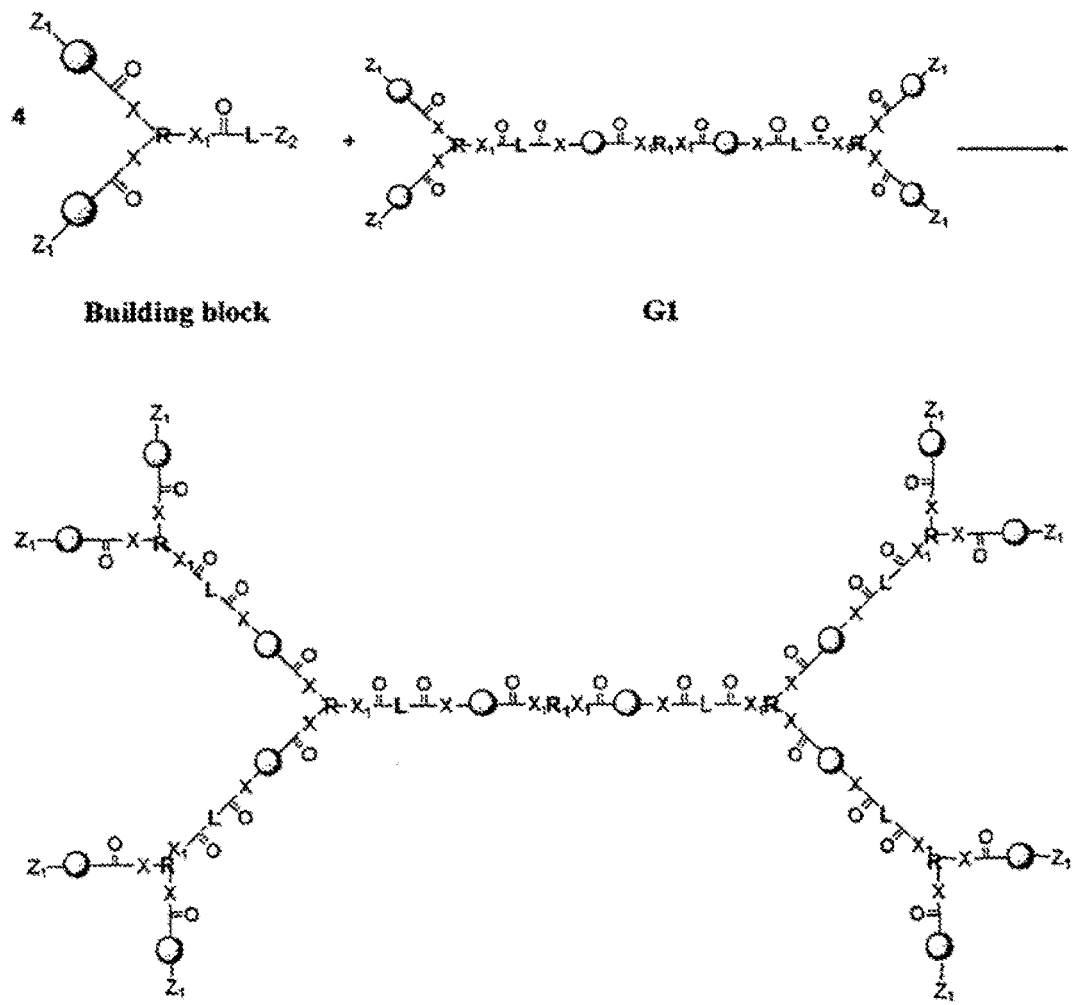
FIG. 22 shows the building block 2400 reacted with $G_1$ 3300 to give the second generation molecule ($G_2$) 3400.
Figure 23:
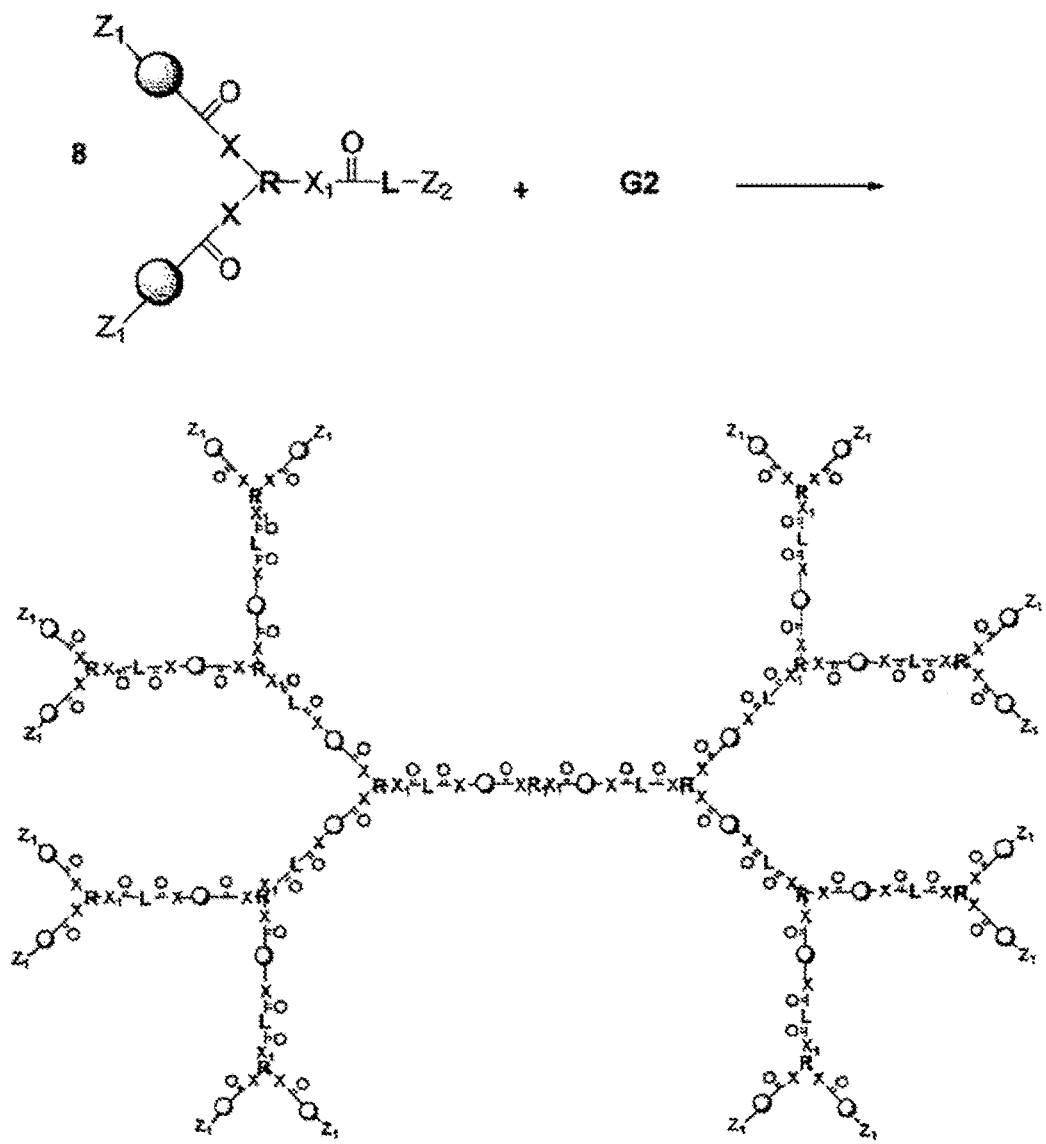
FIG. 23 shows the building block 2400 reacted with $G_2$ 3400 to give the third generation dendritic drug ($G_3$) 3500.

The building block 2400 is reacted with the new core 3200 to give the first generation dendritic drug 3300 shown in FIG. 21 and the building block 2400 is reacted with the first generation molecule 3300 to give the second generation molecule 3400 as shown in FIG. 22, while the building block 2400 is reacted with the second generation compound 3400 to give the third generation 3500 as is shown in FIG. 23. The various constituents are summarized in Table IV.

Preparation of a First Generation Dendritic Drug

EXAMPLE 1

Figure 24A:
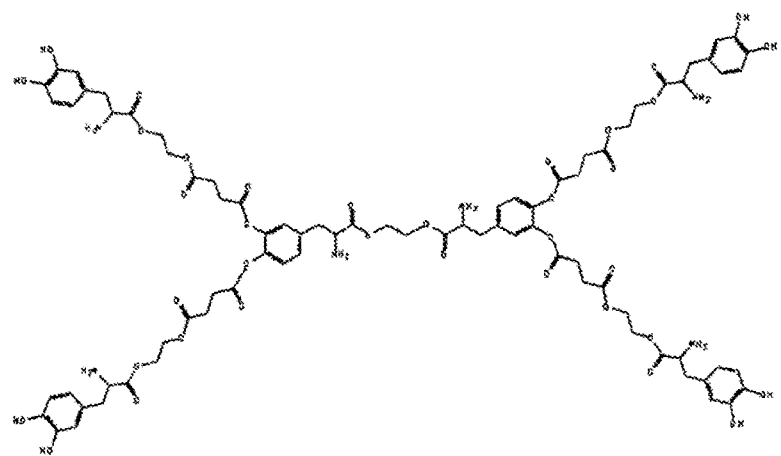
FIG. 24A shows the structure of a first generation dendritic drug made from L-DOPA (HO-$G_1$-$NH_2$).
Figure 24B:
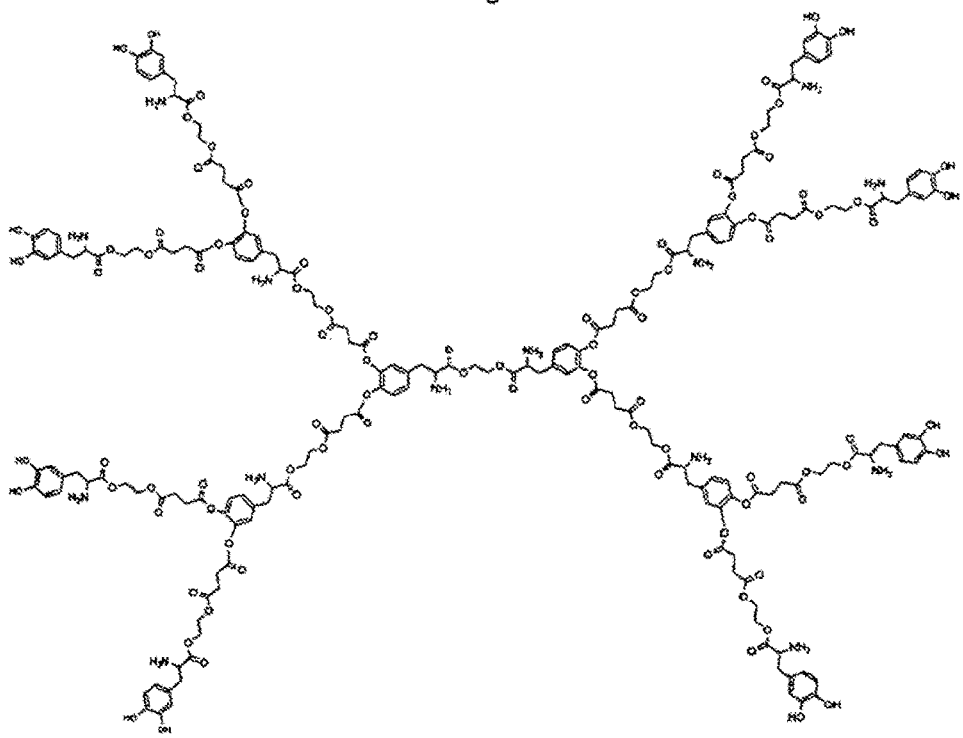
FIG. 24B shows the structure of a second generation dendritic drug.
Figure 24C:
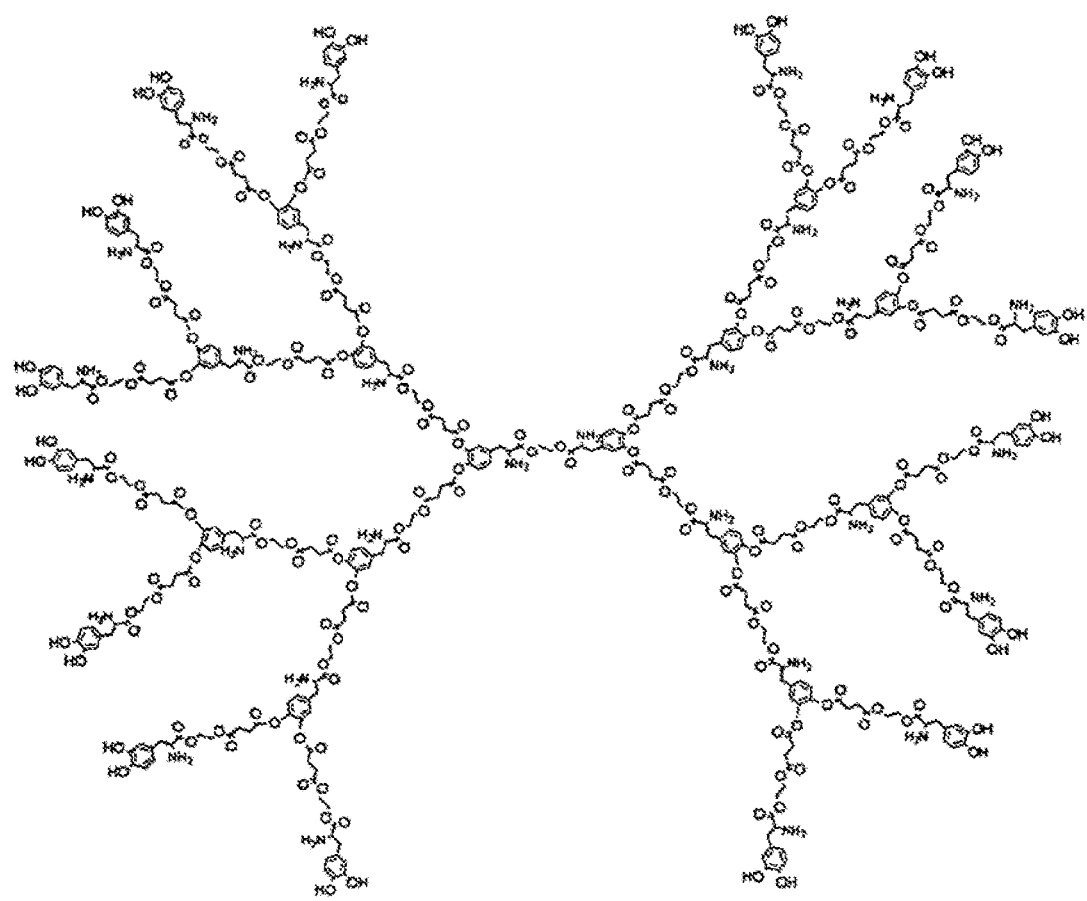
FIG. 24C shows the structure of a third generation dendritic drug.

This example deals with a novel preparation method to form multiple drug units into a cascade structure to form a first generation dendritic drug as shown in FIG. 24.

EXAMPLE 1a

Figure 25:
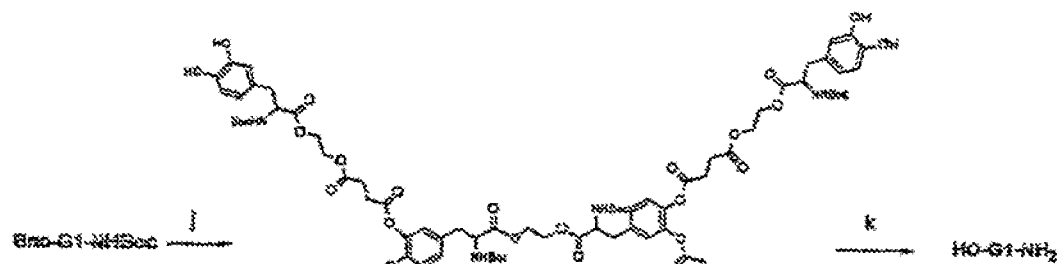
FIG. 25 is the chemical formula for L-Dopa.
Figure 25:
Figure 25:
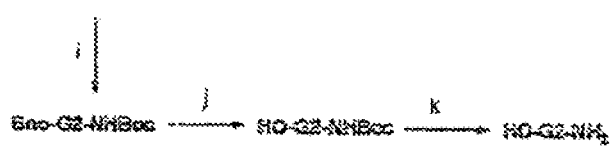
Figure 25:
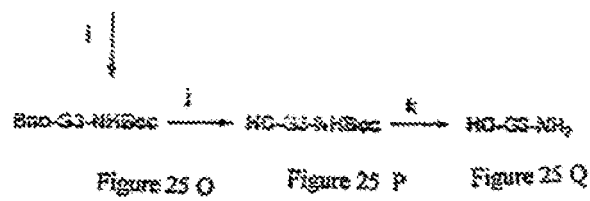

Formation of HO-DOPA-NH$_2$-COOMe (FIG. 25A)

The reaction sequence beings with commercially available L-DOPA (FIG. 25) which was converted to the hydrochloride.

Methanol, 20 ml was cooled to 0° C. and then thionyl chloride (0.89 ml, 12.2 mmol) was slowly added. After 30 minutes, L-Dopa (2.00 g, 10.1 mmol) was slowly added. The mixture was allowed to return to room temperature and was stirred for another 18 hours at room temperature. The mixture was concentrated in vacuo to give a light yellow powder. The solid did not need further purification and was utilized to continue the next reaction.

EXAMPLE 1b

Formation of HO-DOPA-NH-Boc-COOMe (FIG. 25B)

The yellow powder of example 1a (1.000 g, 4.74 mmol) was dissolved in tetrahydrofuran (10 ml) and a solution of 1M NaHCO$_3$ (10.0 ml, 10.0 mmol) was added. The resulting solution was cooled at 0° C., and di-tertbutyl-dicarbonate (1.093 g., 5.0 mmol) was added slowly. The solution was stirred at 0° C. for 1 hour, and then warmed to room temperature and it was stirred for another one hours at room temperature. The organic solvent was removed by vacuum and the aqueous layer was extracted using ethyl acetate (3×10 ml). All organic fractions were combined. The organic layer was washed respectively with water (2×20 ml), 5% HCl (2×20 ml), water (20 ml), brine (20 ml), and dried over MgSO$_4$ and the solvent was removed using vacuum. Further purification was performed using flash chromatography with the eluent: 1: 1 ethyl acetate hexane. The pure product was retrieved as a white solid (1.315 g.).

EXAMPLE 1c

Formation of Benzyl-DOPA-NH-Boc-COOMe (FIG. 25C)

The white powder of example 1b 1.31 g., 4.17 mmol) was dissolved in acetone (15 ml). Potassium carbonate (2.881 g, 20.85 mmol) and sodium iodide (125 mg, 0.83 mmol) were added to the solution. Benzyl bromide (BnBr) (2.25 ml, 18.76 mmol) was added and then the mixture was refluxed at 50° C. for 18 hours. The solvent was removed in vacuo and the sediment was dissolved in Dichloromethane(DCM) (30 ml) and then filtered. The organic phase was washed with water (2×30 ml), 5% HCl (2×30 ml), water(30 ml), brine (30 ml), respectively, and then was dried over $MgSO_4$. The liquid was concentrated to result in a brown oil. Purification was done by flash chromatography with the eluent: 1:3 ethyl acetate:hexane, which gave a white powder (1.800 g.) of the product.

EXAMPLE 1d

Formation of Benzyl-DOPA-NHBoc-COOH (FIG. 25D)

The white powder of example 1c (1.000 gm, 2.04 mmol) was dissolved in a solution (10 ml) of 1:1 tetrahydrofuran to methanol, and 1 M NaOH solution (5 ml) was added to the above solution. The mixture was stirred at room temperature for 6 hours. The mixture was poured in pH=3 $KHSO_4$ aqueous solution (30 ml) and then extracted three times with ethyl acetate (10 ml, 10 ml, 10 ml). The combined organic phase was washed with water (30 ml), and brine (30 mol), and dried over $MgSO_4$. The liquid was concentrated and afforded a white solid (868 mg) as the product.

EXAMPLE 1e

Formation of Benzyl-DOPA-NHBoc-COOCH$_2$CH$_2$OH (FIG. 25E)

The white powder of Example 1d (200 mg, 0.42 mmol) was dissolved in dichloromethane (DCM) (10 ml), and ethylene glycol (0.11 ml, 1.89 mmol), 4-(dimethylamino) pyridinium p-toluenesulfonate (DPTS) (81.9 mg, 0.42 mmol), and 1,3-dicyclohexylcarbodiimide (DCC) (1M in dichloromethane) (0.5 mL 0.5 mmol) was added in a dropwise manner. The solution was stirred at room temperature for 18 hours. The by-product precipitate (dicyclohexyl urea) was filtered and the organic layer was washed with water (2×10 ml), 5% HCl (2×10 ml), water (2×10 ml), saturated NaHCO$_3$ (2×10 ml), water (1×10 ml), brine (1×10 ml), respectively, and then dried over MgSO$_4$. After the solvent was removed in vacuo, flash chromatography was used with the eluents: 1:2 and then 1:1.5 ethyl acetate to hexane mixed solvents, that afforded a colorless solid as the product (180 mg.).

EXAMPLE 1f

Formation of Benzyl-DOPA-NHBoc-linker (FIG. 25F)

The colorless solid of example 1e (3.910 g., 7.5 mmol) was stirred in pyridine (20 ml). A solution of succinic anhydride (1.125 mg, 11.25 mmol) in pyridine (20 ml) was added to the previous solution. The mixed solution was stirred at room temperature for 18 hours. The solvent was removed in vacuo. The sediment was dissolved in dichloromethane (DCM) (30 ml) and washed with 5% HCl (20 ml), water (2×30 ml), brine (30 ml), and then dried over MgSO$_4$. After the organic solvent was removed in vacuo, flash chromatography was applied for purification with the eluents: first 1:2, and then 1:1 ethyl acetate to hexane mixed solvents, that generated a white solid product (3.120 g.).

EXAMPLE 1g

Formation of Bno-G0-NHBoc (FIG. 25G)

The white solid product of example 1f (1.163 g., 2.43 mmol) was stirred with ethylene glycol (50 mg, 0.81 mmol), 4-(dimethylamino) pyridinium p-toluenesulfonate (DPTS) (473 mg, 2.43 mmol) and 1,3-dicyclohexylcarbodiimide (DCC)(1M in dichloromethane) (2.43 ml, 2.43 mmol) in dichloromethane (10 ml) at room temperature for 18 hours. The precipitate (dicyclohexyl urea by-product) was filtered out. The organic layer was washed with water (2×10 ml), 5% HCl (2×10 ml), water (2×10 ml), saturated NaHCO$_3$ (2×10 ml), water (2×10 ml), and brine (10 ml), respectively, and then dried over MgSO$_4$. After the solvent was removed in vacuo, flash chromatography was used to purify the product with the eluent: 1:2 ethyl acetate to hexane mixed solutions, which afforded a colorless solid (836 mg.).

EXAMPLE 1h

Formation of HO-G0-NBBoc (FIG. 25H)

To a solution of the colorless solid of example 1g (836 mg, 0.85 mmol) in tetrahydrofuran (10 ml), 5% palladium on charcoal (100 mg) was added and the mixture was hydrogenated using H$_2$ under a pressure of 50 bars for 4 hours. The mixture was then filtered and the filtrate was concentrated by removing the solvent in vacuo to give a white powder. Flash chromatography was performed with the eluent: 1:1 ethyl acetate to hexane mixed solvents which afforded a white solid (392 mg) as the product.

EXAMPLE 1i

Formation of BnO-G$_1$-NHBoc (FIG. 25I)

The white solid product of example 1 h (246 mg, 0.4 mmol) was stirred with the compound from example 1f (1.184 g. 1.9 mmol), 4-(dimethylamino)Pyridinium p-toluenesulfonate (DPTS)(120 mg., 0.4 mmol), and 1,3-dicyclohexylcarbodiimide (DCC) (1M solution in dichloromethane) (1.9 ml, 1.9 mmol) in dichloromethane (DCM) (10 ml) at room temperature for 18 hours. The mixture was filtered and the organic layer was washed with 5% HCl (2×15 ml), water (2×15 ml), saturated NaHCO$_3$ (2×15 ml), water (2×15 ml), and brine (15 ml), respectively, and then dried over MgSO$_4$. After the solvent was removed in vacuo flash chromatography was applied to purify the product with the eluents: 1:2 and then 1:1 ethyl acetate to hexane mixed solvents, which gave a white solid (400 mg).

EXAMPLE 1j

Formation of HO-G$_1$-NBBoc (FIG. 25J)

The white solid (505 mg, o.17 mmol) was dissolved in tetrahydrofuran (10 ml), 5% palladium on charcoal (100 mg)

was added. The suspension was charged with hydrogen (50 bars) and agitated for 6 h. The mixture was then filtered, and the filtrate was evaporated in vacuo. Purification by a column chromatography, eluent: 1:1 and then 2:1 ethyl acetate to hexane mixed solvent, afforded product as a white solid (354 mg).

EXAMPLE 1k

Formation of Example HO-G1-NH2 (FIG. 24A)

The white solid (180 mg) was stirred in 2 ml of 4M HCl in dioxane at room temperature for 5 minutes. The solvent and the remaining HCl was removed in vacuo and the white sediment was washed with DCM (2×1 ml). After drying, the product was afforded as a colorless powder (130 mg).

Similarly, HO-G2-NH$_2$ and HO-G3-NH$_2$ can be accessed as showed in FIG. 24B and 25C, respectively.
a=SOC$_2$, MeOH, rm, 18 h;
b=Boc$_2$O, TIF, 1M Na$_2$CO$_3$, 0° C., 2 h, 90%
c=BnBr, K$_2$CO$_3$, acetone, reflux, 18 h, 79%
d=MeOH/THF, 1M NaOH, 6 h, rm, 93%
e=4.5 equ. ethylene glycol, DCC, DPTS, DCM, rm, 6 h, 86%
f=succinic anhydride, pyridine, rm, 18 h, 68%
g=0.5 eq. ethylene glycol, DCC, DPTS, DCM, rm, 16 h, 78%
h=THF, 5% Pd/C, 50 bars H$_2$, 4 h, 94%
i=DCC, DPTS, DCM, rm, 18 h, 76% G$_1$, 72% G$_2$, 68% G$_3$
j=THF, 5% P/C, 50 bars H$_2$, 6 h, 92% G$_1$, 90% G$_2$/G$_3$,
k=4N HCl/Dioxane, rm, 5 minutes, 87% G$_1$, 86% G$_2$, 82% G$_3$.

EXAMPLE 2

Synthesis of ACP Dendrimer

Using aspirin as the starting drug, an ACP dendrimer drug was prepared by the schematic representation described infra. Abbreviations and acronyms are defined throughout this specification.
Step 1 Construction of building block and G0 (core):

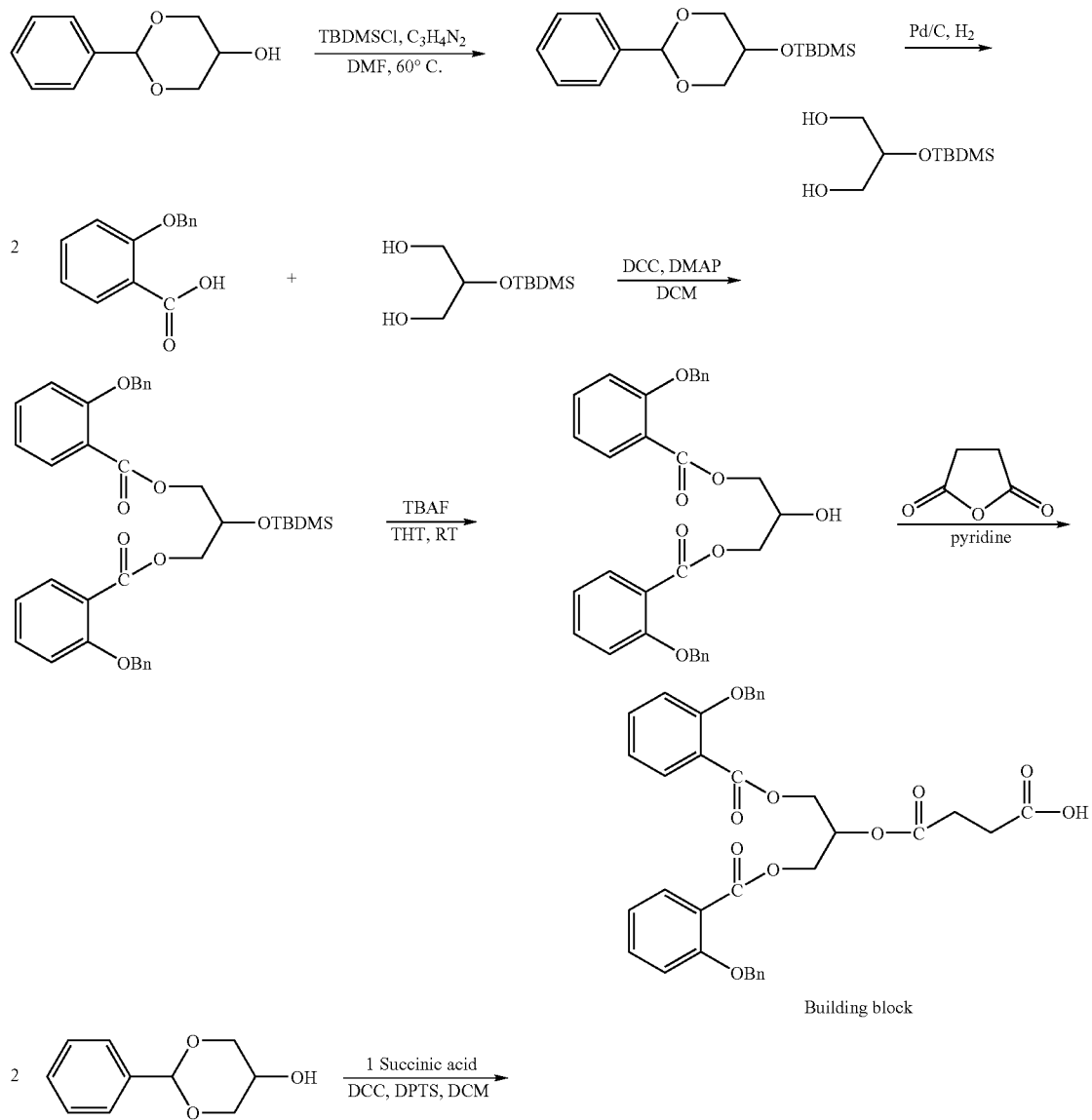

Building block

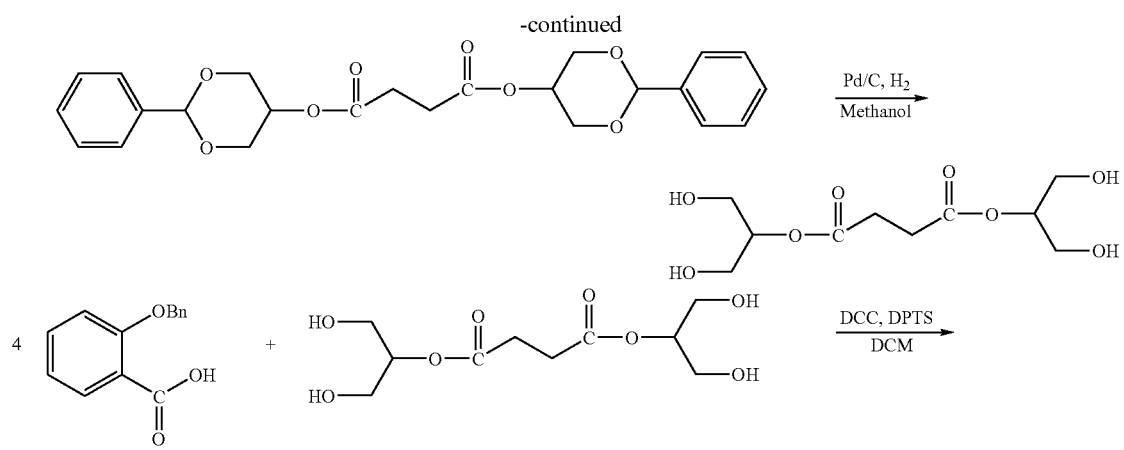
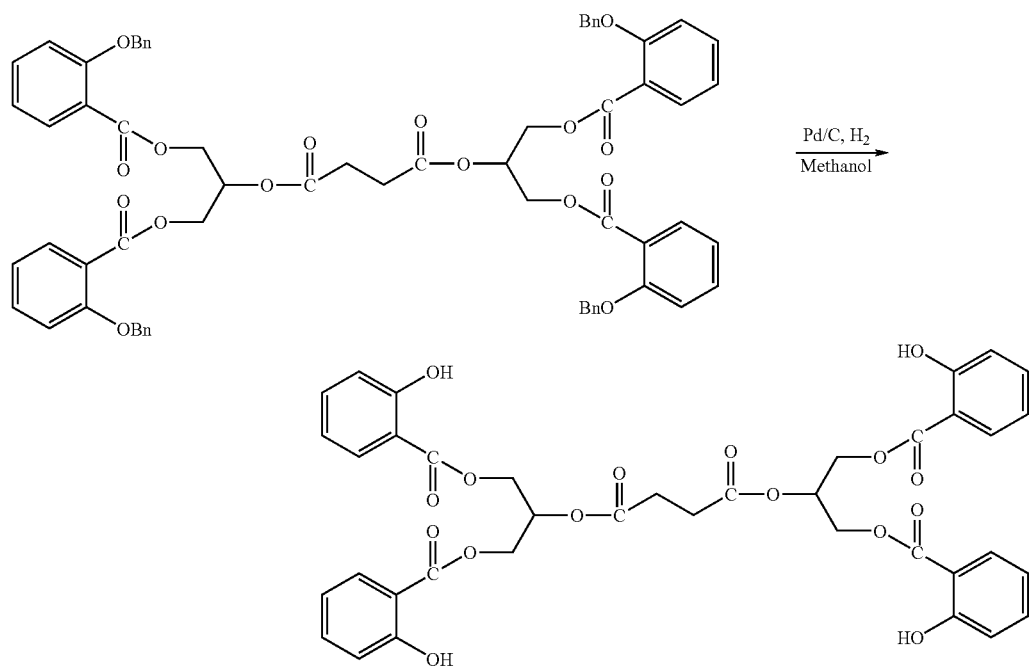
G0 (Core)
The synthesis of Generations $G_1$, $G_2$, and $G_3$, follow.
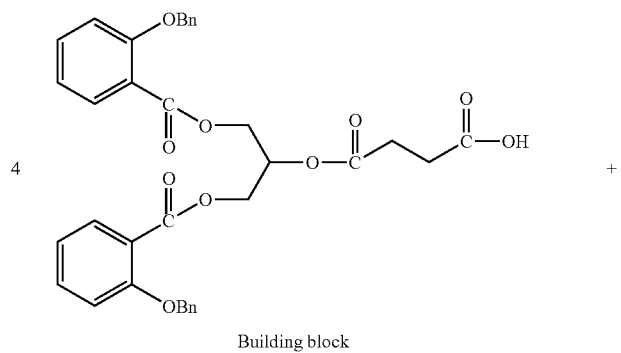
Building block

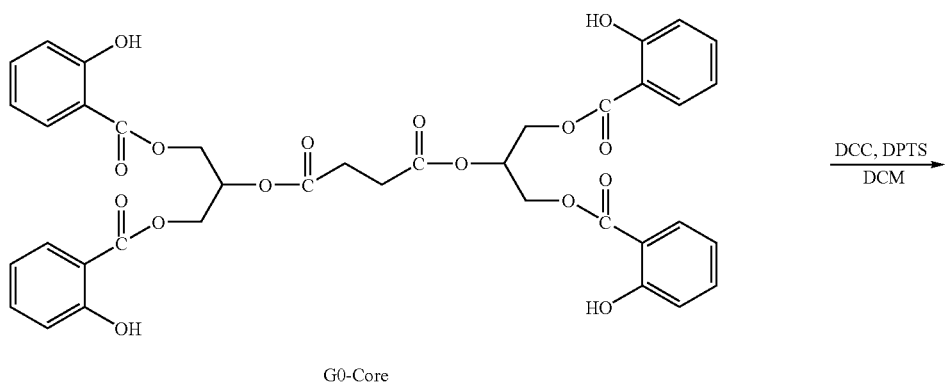
G0-Core
$\xrightarrow{\text{DCC, DPTS}}_{\text{DCM}}$
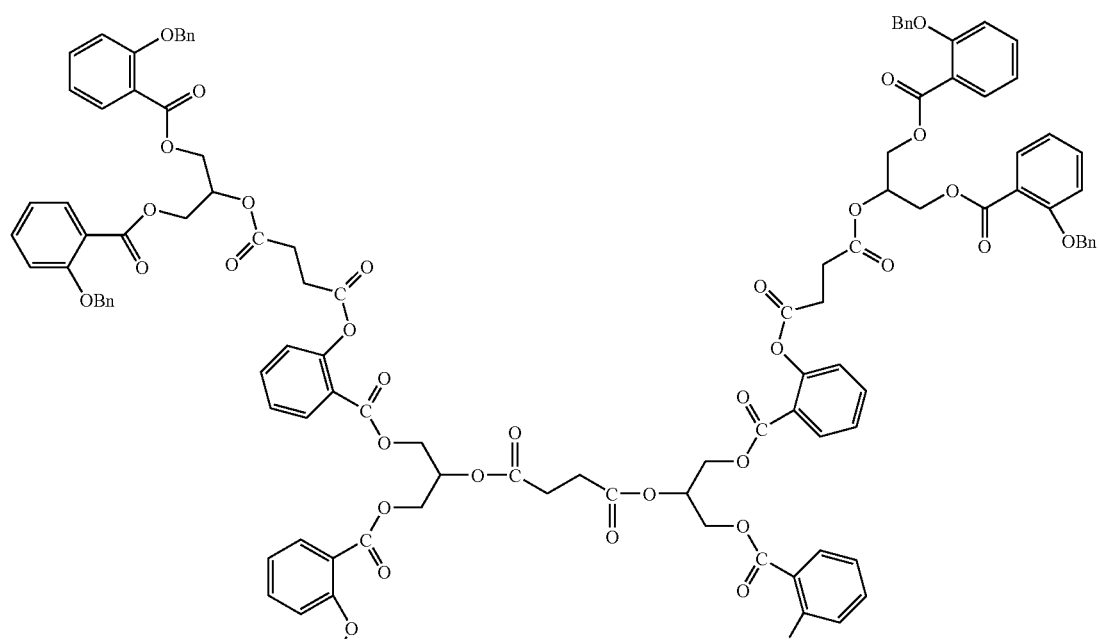
BnO-G1
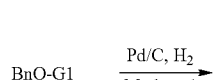
BnO-G1 $\xrightarrow{\text{Pd/C, H}_2}_{\text{Methanol}}$

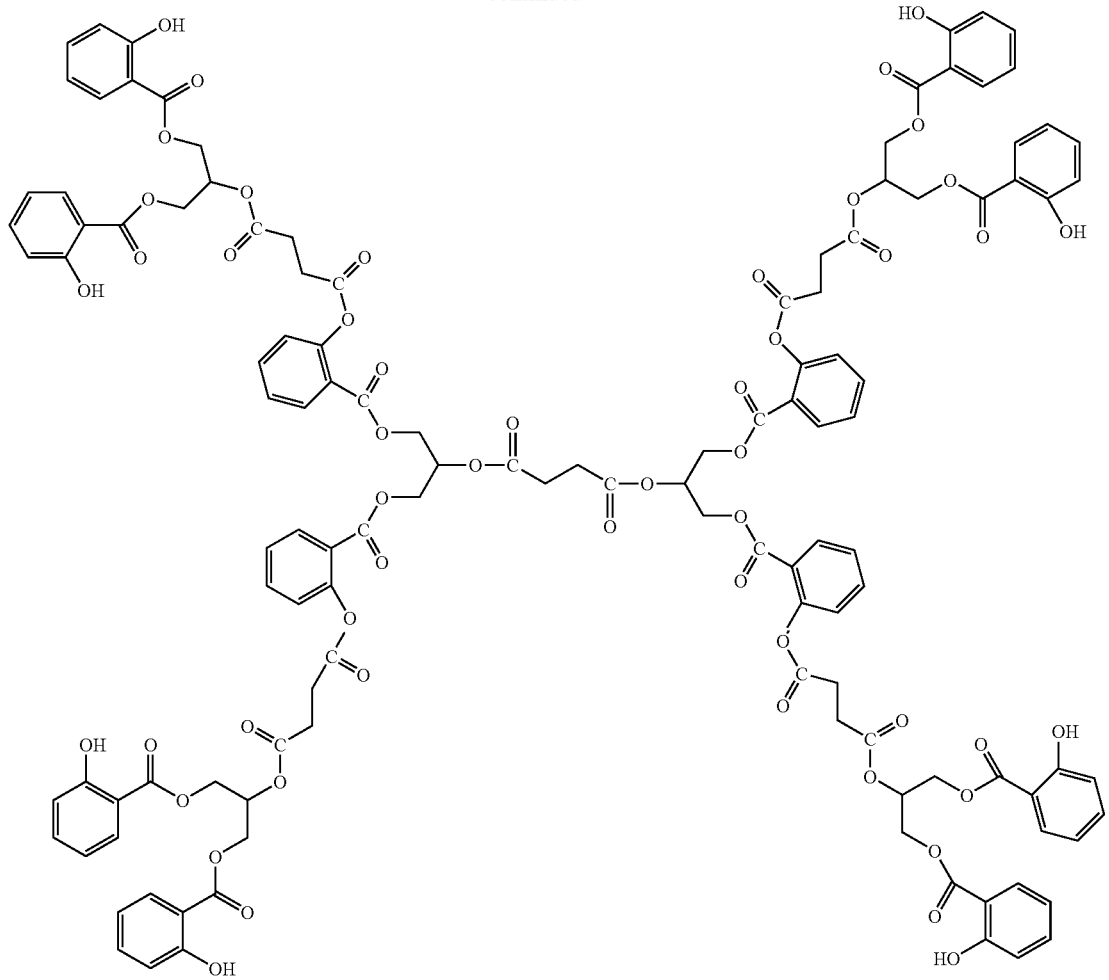
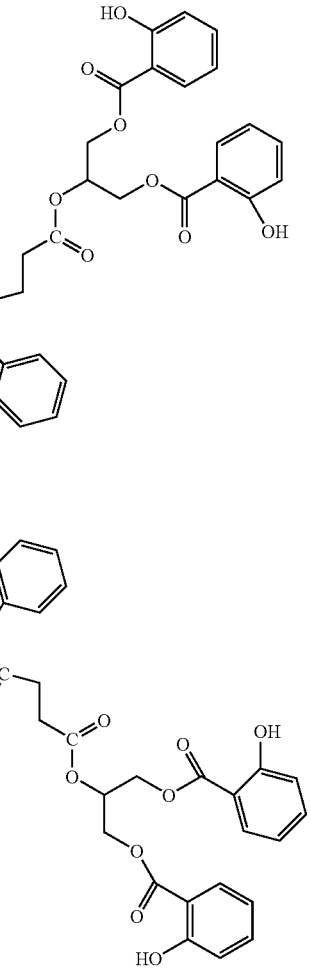
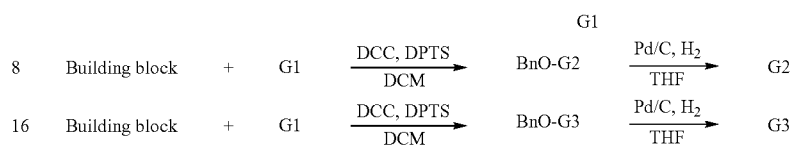
EXAMPLE 4
Preparation of a Multiple Drug Dendrimer
The following is the preparation of a multiple drug dendrimer provided in a schematic form. Abbreviations and acronyms are defined elsewhere in this specification.
I. Drugs Protection
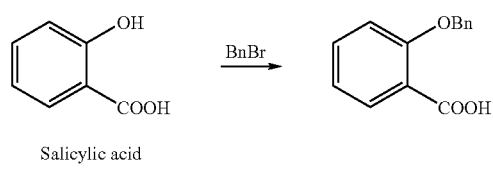
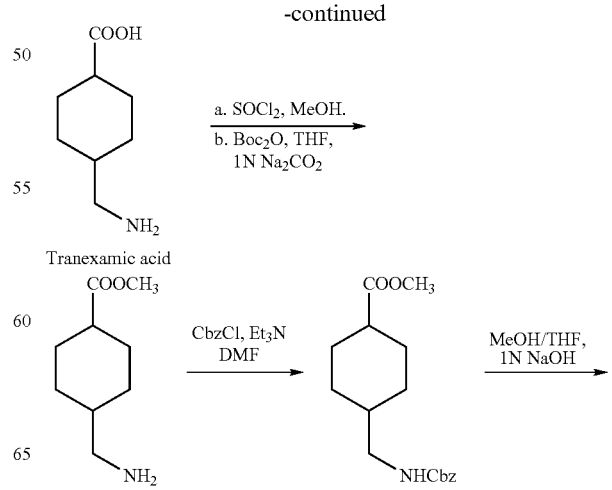

25
-continued
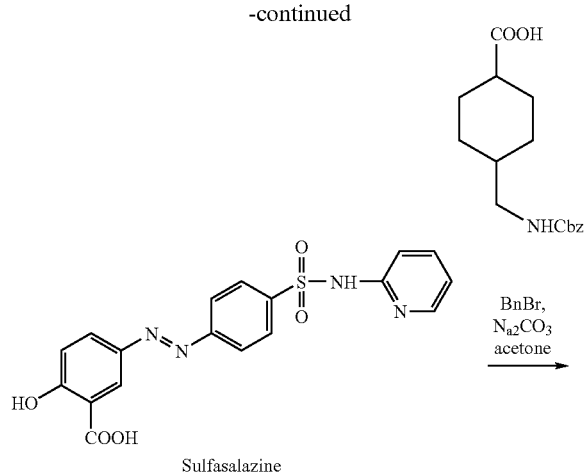
Sulfasalazine
26
-continued
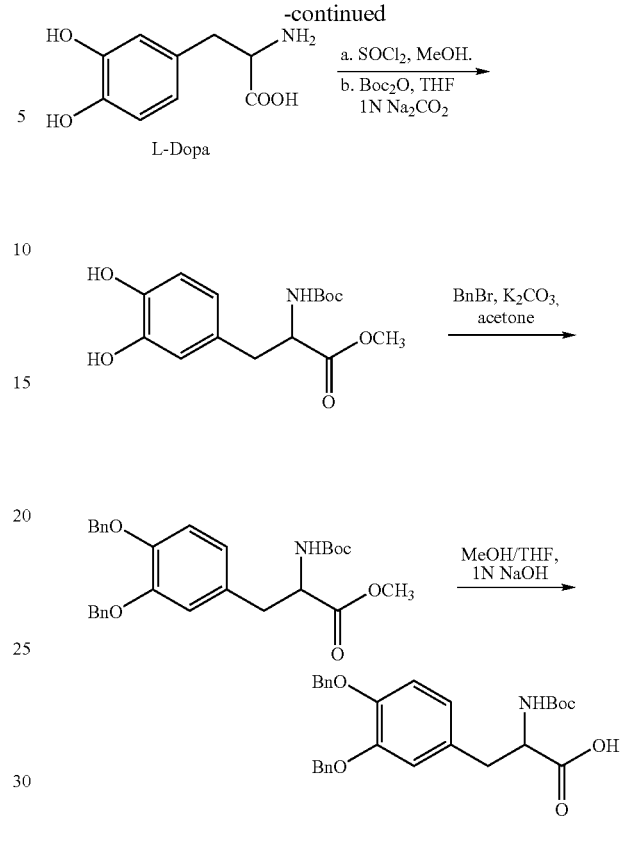
L-Dopa
II. Pre-core and Pre-linker Preparations
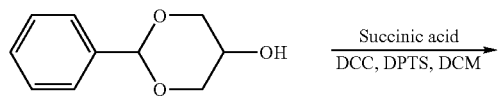
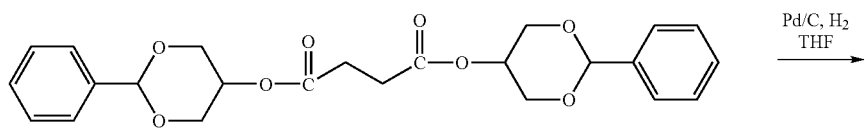
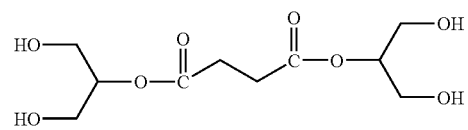
Pre-core (G0.5)
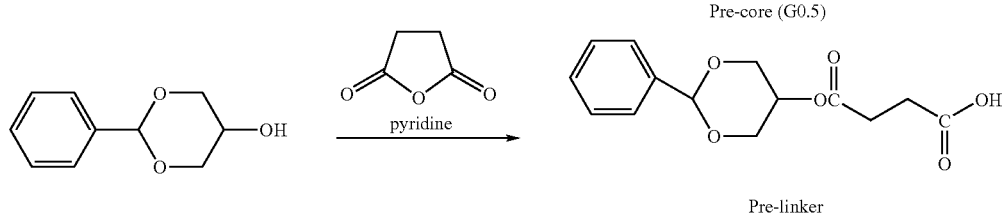
Pre-linker

III. First Drug Coupling
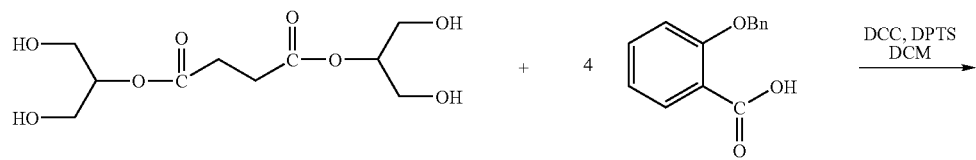
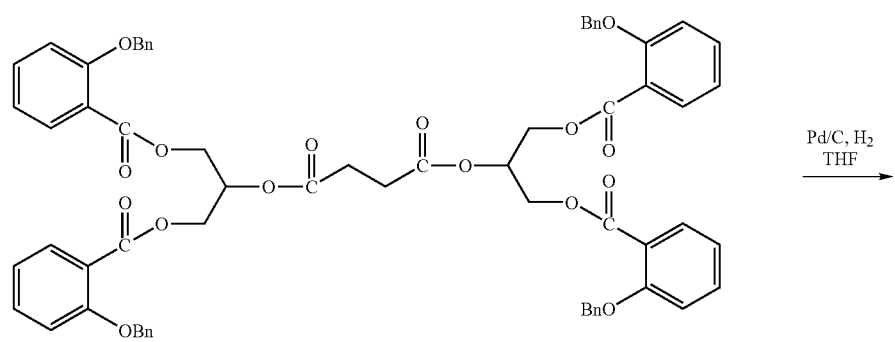
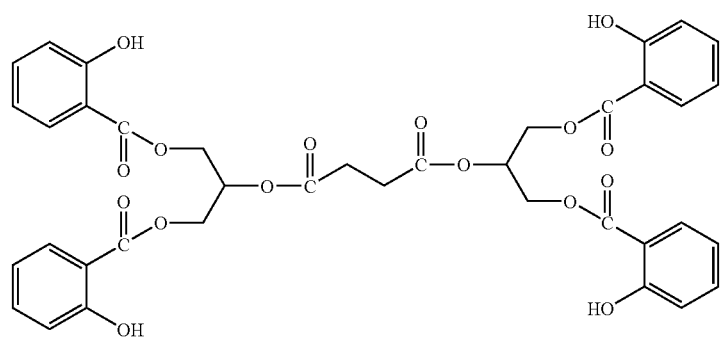
Core (G0)
IV. Second Drug Coupling
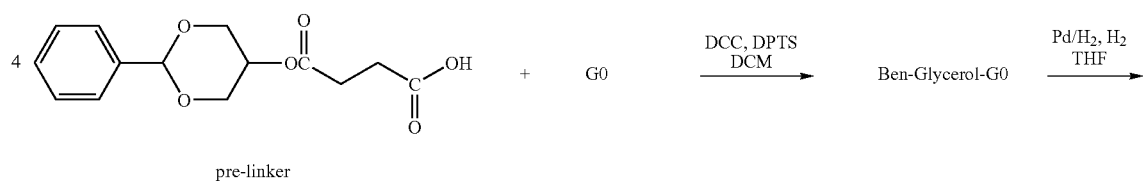
pre-linker

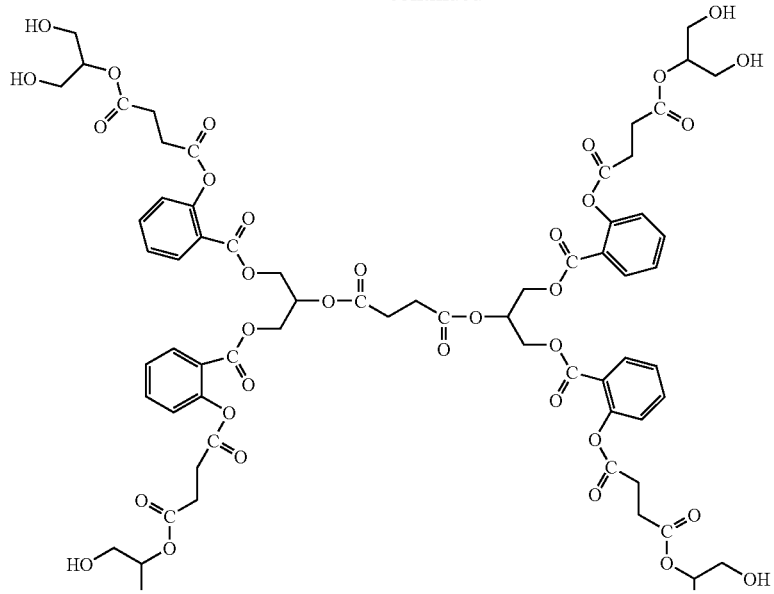
G0.5
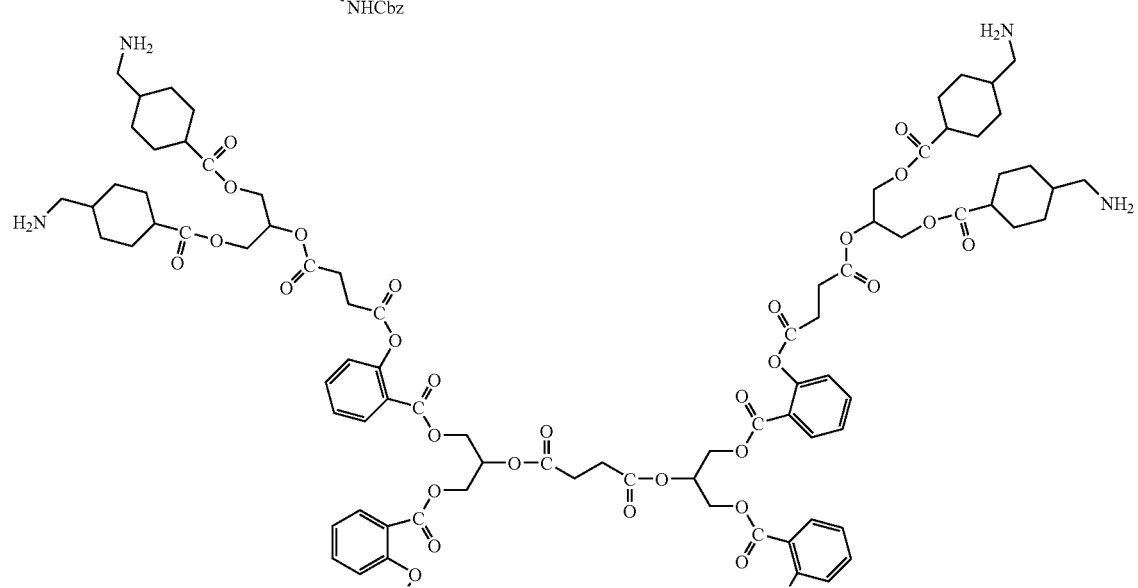

31 32
-continued
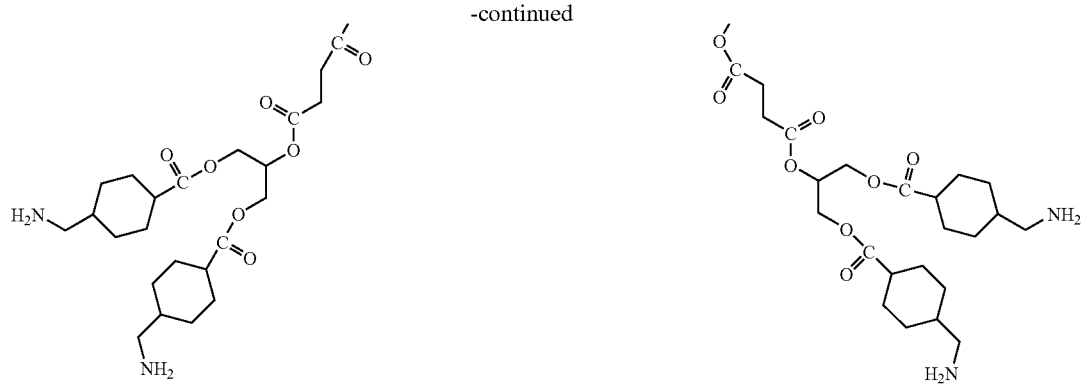
G1
V. Third Drug Coupling
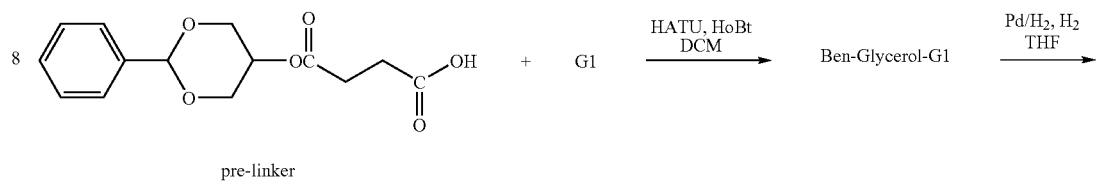
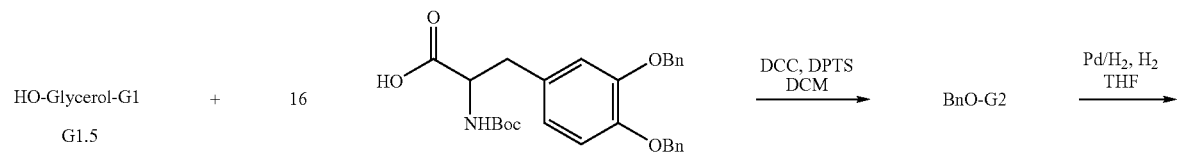
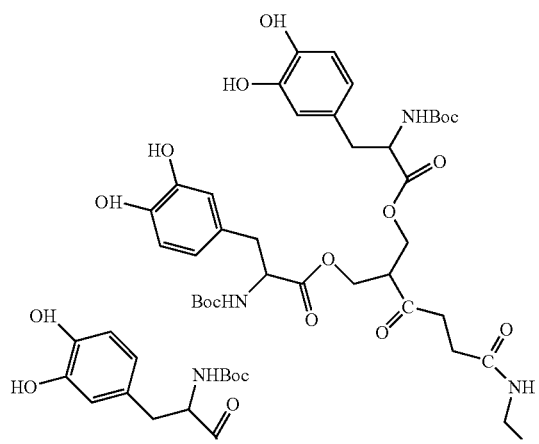

-continued
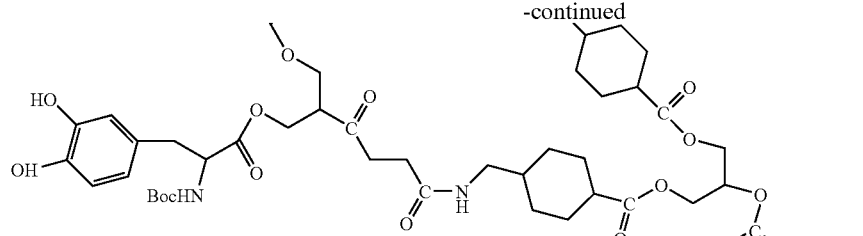
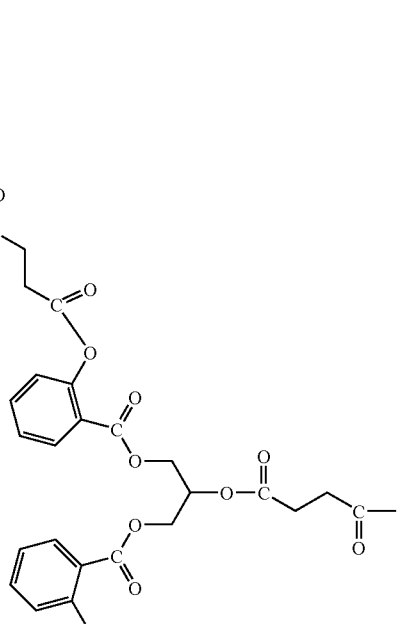
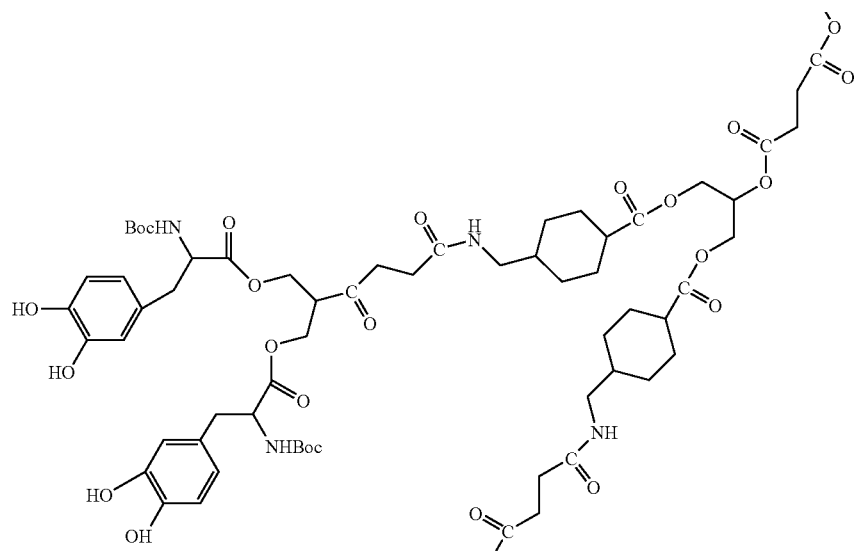
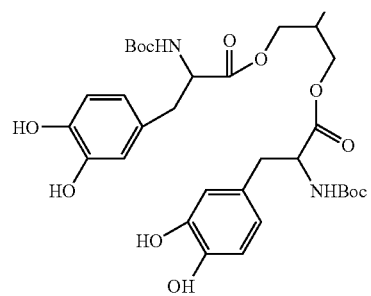

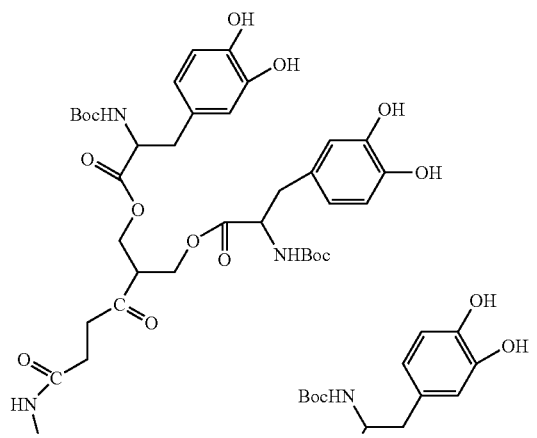
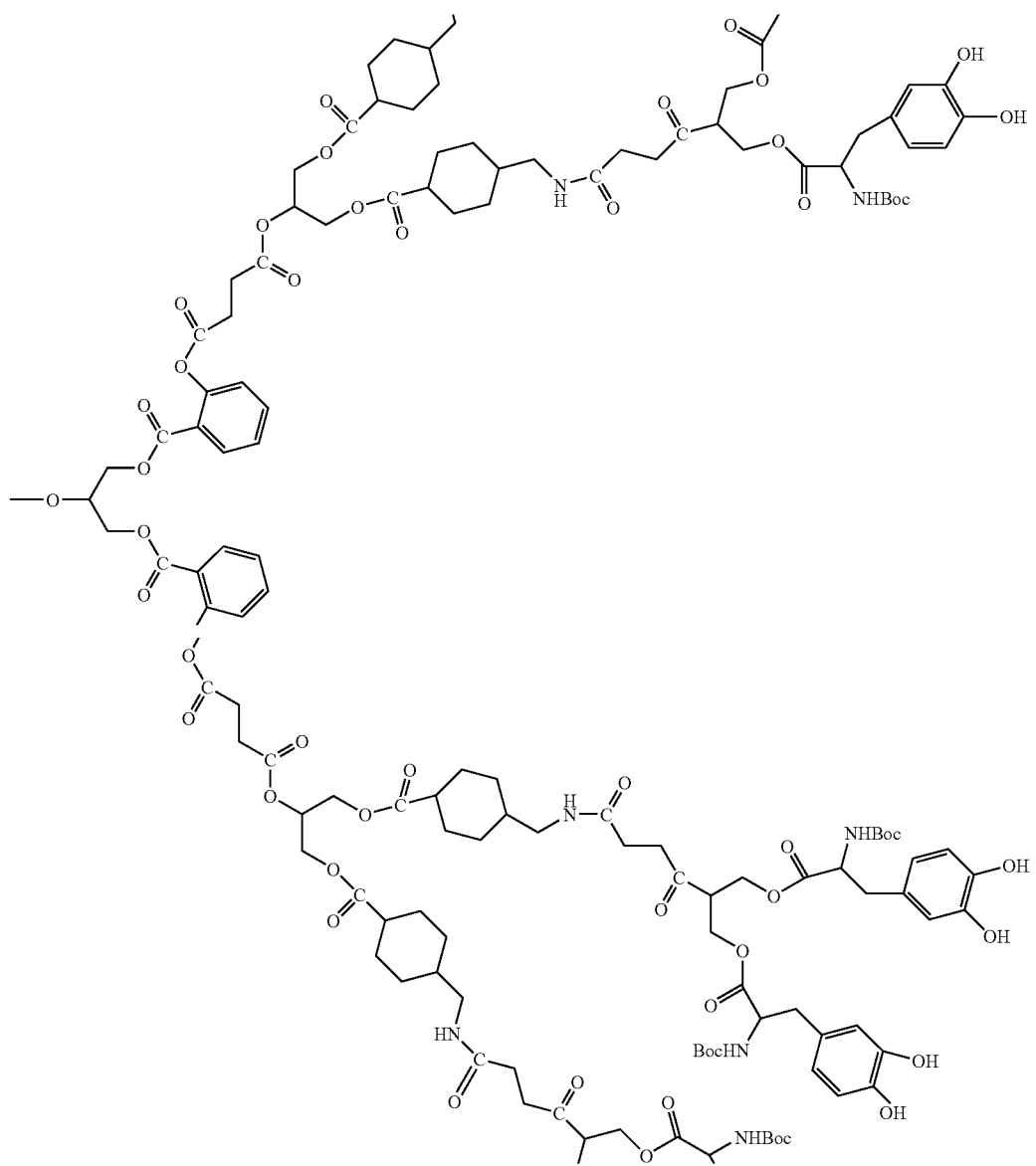

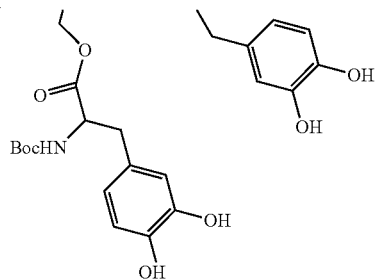
Boc-G2
VI. Fourth Drug Coupling
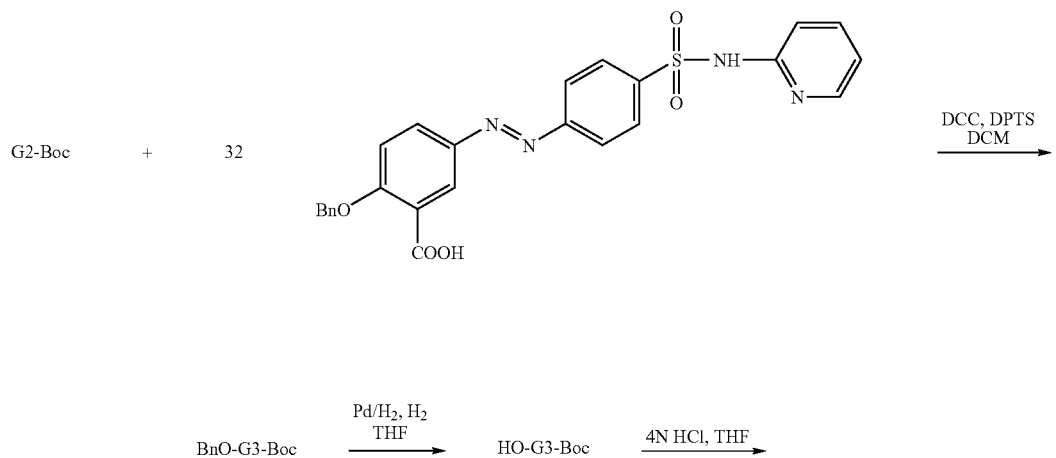
BnO-G3-Boc $\xrightarrow{\text{Pd/H}_2, \text{H}_2}{\text{THF}}$ HO-G3-Boc $\xrightarrow{\text{4N HCl, THF}}$
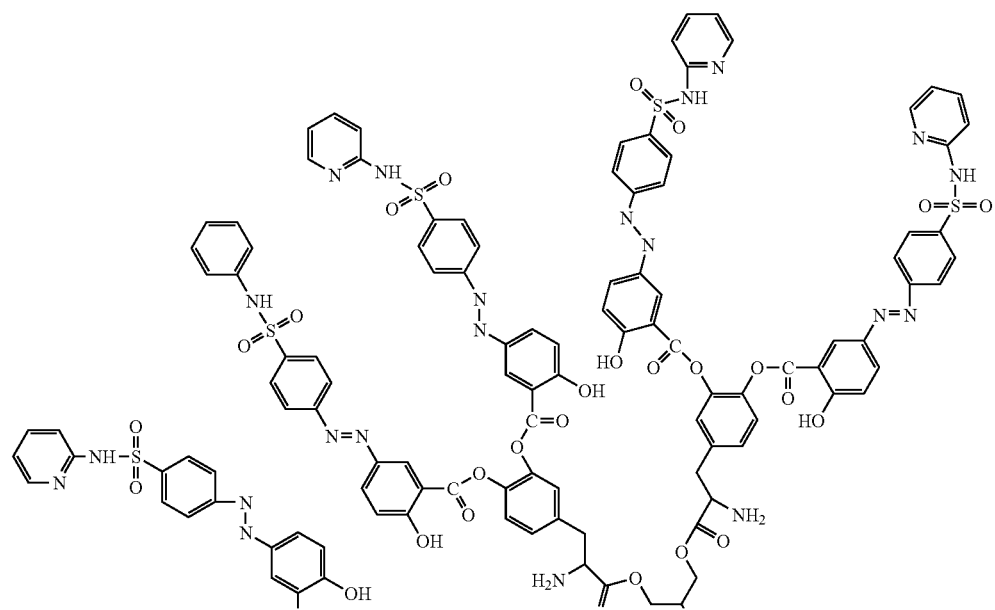

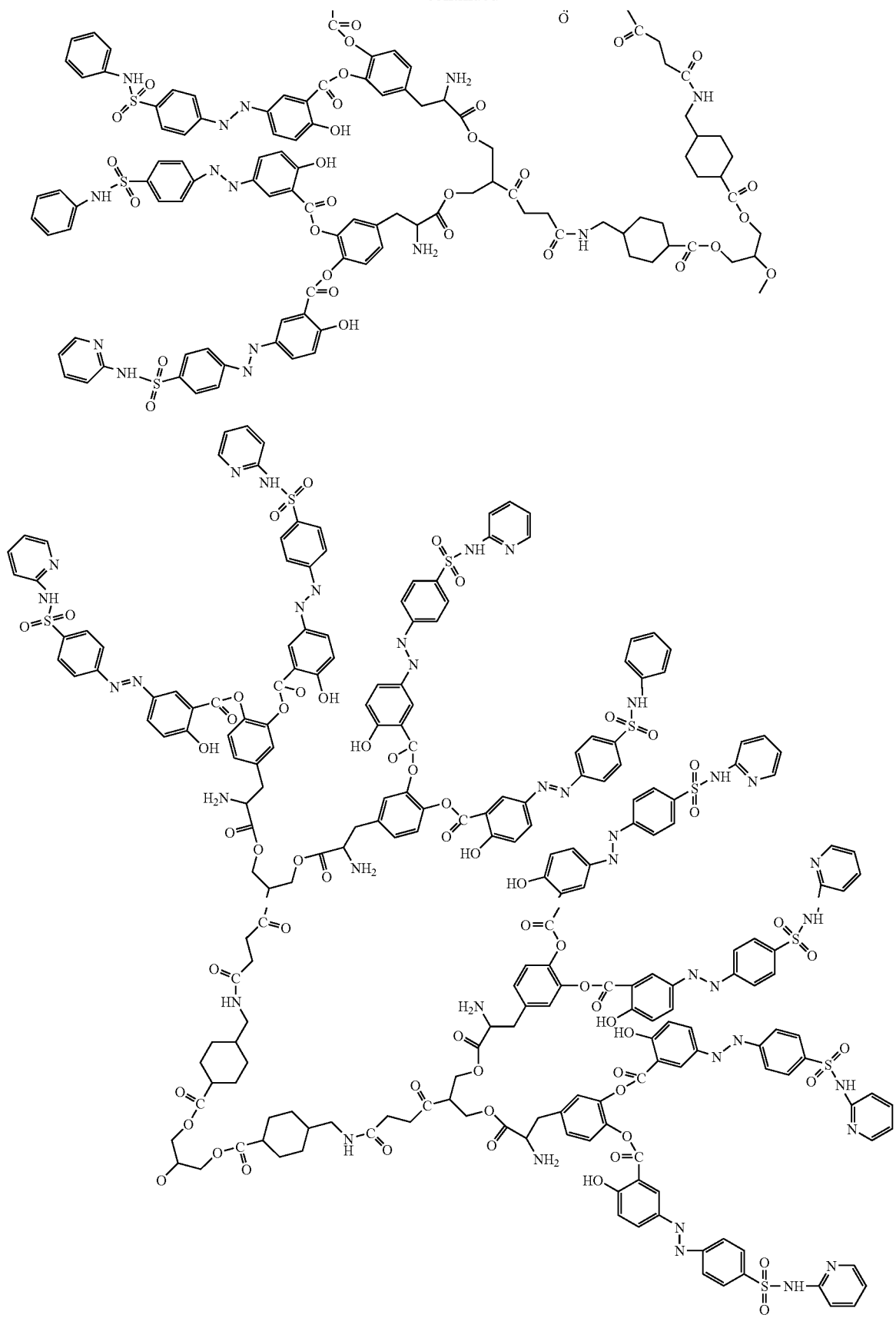

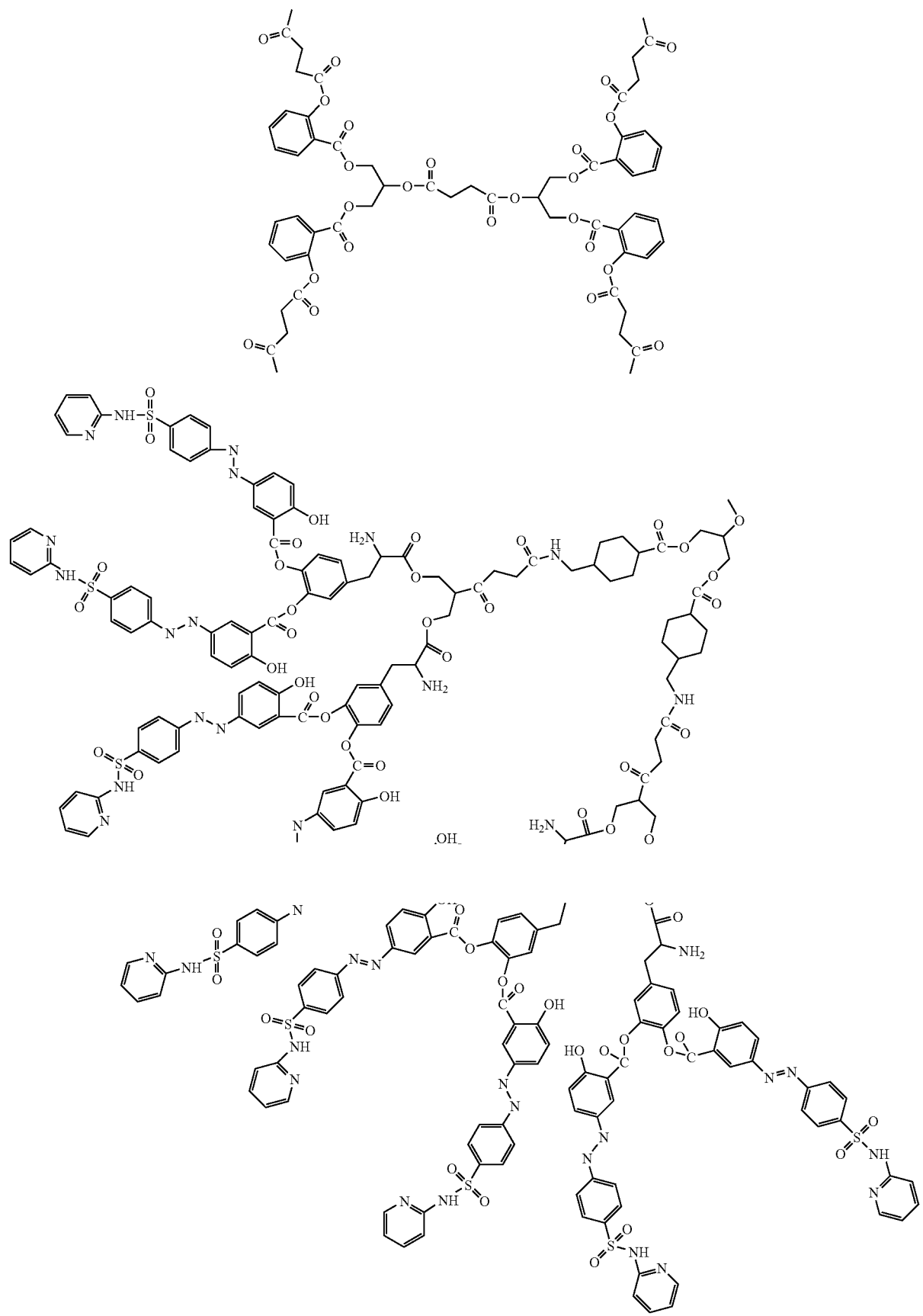

-continued

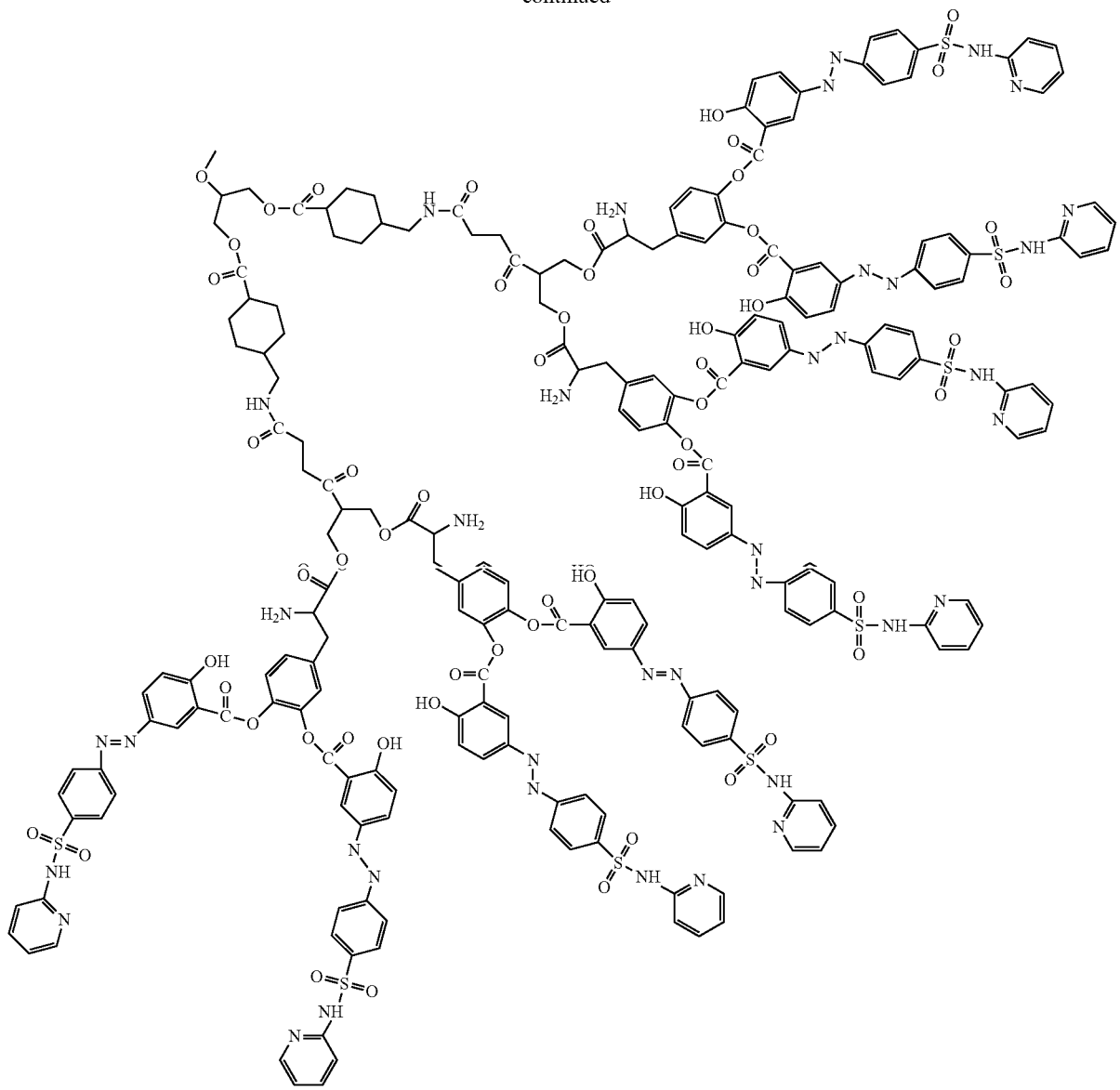

Multiple-drug Dendrimer (MDD, G3)

What is claimed is:

1. A method of preparing a dendritic drug, the method comprising:
(I) providing a therapeutically active multifunctional drug, said drug having at least one reactive group capable of providing a linker site, said drug having at least one functional group capable of providing a starting point for the preparation of a dendritic structure;
(II) chemically protecting any reactive group in the drug that is not capable of providing a linker site or providing a starting point for the preparation of a dendritic molecule;
(III) chemically protecting any reactive groups capable of providing a linker site;
(IV) chemically protecting any functional group capable of providing a starting point for the preparation of a dendritic molecule;
(V) deprotecting any group formed in (III);
(VI) reacting any group formed in (V) with a first linker group selected from the group consisting of:
(i) biologically compatible compounds,
(ii) biologically inactive compounds,
(iii) biologically active compounds,
(iv) biologically compatible and bioactive compounds,
(v) biologically compatible and biologically inactive compounds;
(VII) reacting the first linker from (VI) with a second linker group selected from the group consisting of:
(i) biologically compatible compounds,
(ii) biologically inactive compounds, (iii) biologically active compounds,
(iv) biologically compatible and bioactive compounds,
(v) biologically compatible and biologically inactive compounds;
(VIII) coupling two units formed in (VI) through the first linker groups;
(IX) deprotecting the groups formed in (IV) to yield a core molecule for the dendritic drug;
(X) reacting a predetermined amount of the molecules formed in (VI) with each one equivalent of the molecule formed in (VIII), and deprotecting the protected groups formed in (IV);
(XI) deprotecting any group in the molecule that is not capable of providing a linker site or providing a starting point for the preparation of a dendritic molecule to give a first generation dendritic drug.

2. The method as claimed in claim 1 wherein a lower generation dendritic drug is iteratively treated using steps (X) and (XI) to form a higher generation dendritic drug.

3. The method as claimed in claim 2 wherein dendritic drugs having up to, and including fourteen generations, is obtained.

4. The method as claimed in claim 2 wherein a first generation dendritic drug is treated using steps (X) and (XI) to produce a second generation dendritic drug.

5. The method as claimed in claim 4 wherein the second generation dendritic drug is treated using steps (X) and (XI) to produce a third generation dendritic drug.

6. The method as claimed in claim 5 wherein the third generation dendritic drug is treated using steps (X) and (XI) to produce a fourth generation dendritic drug.

7. The method as claimed in claim 6 wherein the fourth generation dendritic drug is treated using steps (X) and (XI) to produce a fifth generation dendritic drug.

8. The method as claimed in claim 7 wherein the fifth generation dendritic drug is treated using steps (X) and (XI) to produce a sixth generation dendritic drug.

9. The method as claimed in claim 8 wherein the sixth generation dendritic drug is treated using steps (X) and (XI) to produce a seventh generation dendritic drug.

10. The method as claimed in claim 9 wherein the seventh generation dendritic drug is treated using steps (X) and (XI) to produce an eighth generation dendritic drug.

11. The method as claimed in claim 10 wherein the eighth generation dendritic drug is treated using steps (X) and (XI) to produce a ninth generation dendritic drug.

12. The method as claimed in claim 11 wherein the ninth generation dendritic drug is treated using steps (X) and (XI) to produce a tenth generation dendritic drug.

13. The method as claimed in claim 12 wherein the tenth generation dendritic drug is treated using steps (X) and (I) to produce an eleventh generation dendritic drug.

14. The method as claimed in claim 13 wherein the eleventh generation dendritic drug is treated using steps (X) and (XI) to produce a twelfth generation dendritic drug.

15. The method as claimed in claim 14 wherein the twelfth generation dendritic drug is treated using steps (X) and (XI) to produce a thirteenth generation dendritic drug.

16. The method as claimed in claim 15 wherein the thirteenth generation dendritic drug is treated using steps (X) and (XI) to produce a fourteenth generation dendritic drug.

17. A method of preparing a dendritic drug, wherein the dendritic drug has more than one type of drug in the structure, the method comprising:
(I) providing at least two therapeutically active multifunctional drugs, said drugs having at least one reactive group capable of providing a linker site, said drugs having at least one functional group capable of providing a starting point for the preparation of a dendritic structure;
(II) chemically protecting any reactive group in the drugs that are not capable of providing a linker site or providing a starting point for the preparation of a dendritic molecule;
(III) chemically protecting any reactive groups capable of providing a linker site;
(IV) chemically protecting any functional group capable of providing a starting point for the preparation of a dendritic molecule;
(V) deprotecting any group formed in (III);
(VI) reacting any group formed in (V) with a first linker group selected from the group consisting of:
(i) biologically compatible compounds,
(ii) biologically inactive compounds,
(iii) biologically active compounds,
(iv) biologically compatible and bioactive compounds,
(v) biologically compatible and biologically inactive compounds;
(VII) reacting the first linker from (VI) with a second linker group selected from the group consisting of:
(i) biologically compatible compounds,
(ii) biologically inactive compounds,
(iii) biologically active compounds,
(iv) biologically compatible and bioactive compounds,
(v) biologically compatible and biologically inactive compounds;
(VIII) coupling two units formed in (VI) through the first linker groups;
(IX) deprotecting the groups formed in (IV) to yield a core molecule for the dendritic drug;
reacting a predetermined amount of the molecules formed in (VI) with each one equivalent of the molecule formed in (VII), and deprotecting the protected groups formed in (IV);
(XI) deprotecting any group in the molecule that is not capable of providing a linker site or providing a starting point for the preparation of a dendritic molecule to give a first generation dendritic drug.

* * * * *